US010501389B1

(12) United States Patent
Xu et al.

(10) Patent No.: US 10,501,389 B1
(45) Date of Patent: Dec. 10, 2019

(54) PROCESS AND SYSTEM FOR THE PRODUCTION OF PARA-XYLENE AND BENZENE FROM STREAMS RICH IN C6 TO C12+ AROMATICS

(71) Applicant: SAUDI ARABIAN OIL COMPANY, Dhahran (SA)

(72) Inventors: Qi Xu, Dhahran (SA); Raed H. Abudawoud, Khobar (SA); Zhonglin Zhang, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 0 days.

(21) Appl. No.: 16/170,923

(22) Filed: Oct. 25, 2018

(51) Int. Cl.
| | |
|---|---|
| C07C 4/20 | (2006.01) |
| C07C 7/12 | (2006.01) |
| C07C 6/04 | (2006.01) |
| C07C 7/00 | (2006.01) |
| B01J 19/24 | (2006.01) |
| B01J 7/00 | (2006.01) |
| B01D 53/047 | (2006.01) |
| C07C 5/27 | (2006.01) |

(52) U.S. Cl.
CPC .............. *C07C 4/20* (2013.01); *B01D 53/047* (2013.01); *B01J 7/00* (2013.01); *B01J 19/245* (2013.01); *C07C 5/277* (2013.01); *C07C 6/04* (2013.01); *C07C 7/005* (2013.01); *C07C 7/12* (2013.01); *B01D 2256/16* (2013.01); *B01D 2257/7022* (2013.01)

(58) Field of Classification Search
CPC ......... C07C 15/08; C07C 6/126; C07C 6/123; C07C 5/2732; C07C 6/06; C07C 5/277; C07C 6/12; C07C 15/06; C07C 2/66; C07C 15/24; C07C 15/00; B01J 19/24; B01J 29/076; B01J 29/48; B01J 37/18; B01J 35/026; B01J 8/04
See application file for complete search history.

(56) References Cited

U.S. PATENT DOCUMENTS

| | | | |
|---|---|---|---|
| 4,013,734 A | 3/1977 | Kim | |
| 4,127,471 A | 11/1978 | Suggitt et al. | |
| 4,172,813 A | 10/1979 | Bertolacini et al. | |
| 4,310,715 A | 1/1982 | Dorawala et al. | |
| 5,004,854 A | 4/1991 | Yan | |
| 5,030,787 A | 7/1991 | Absil et al. | |
| 5,763,720 A | 6/1998 | Buchanan et al. | |
| 5,847,256 A | 12/1998 | Ichioka et al. | |
| 5,866,741 A | 2/1999 | Wu et al. | |
| 5,942,651 A | 8/1999 | Beech, Jr. et al. | |
| 5,952,536 A | 9/1999 | Nacamuli et al. | |
| 6,096,938 A | 8/2000 | Ghosh | |
| 6,204,422 B1 | 3/2001 | Tsutsui et al. | |
| 6,359,184 B1 | 3/2002 | Kato et al. | |
| 6,706,937 B2 | 3/2004 | Xiao et al. | |
| 7,288,687 B1 | 10/2007 | Frey et al. | |
| 7,544,849 B2 | 6/2009 | Boldingh et al. | |
| 7,563,358 B2 | 7/2009 | Stavens et al. | |
| 7,663,010 B2 | 2/2010 | Levin | |
| 7,727,490 B2 | 6/2010 | Zhou | |
| 8,071,828 B2 | 12/2011 | Cao et al. | |
| 8,084,657 B2 | 12/2011 | Kong et al. | |
| 8,183,424 B2 | 5/2012 | Levin et al. | |
| 8,198,502 B2 | 6/2012 | Bresler et al. | |
| 8,431,758 B2* | 4/2013 | Frey ...................... | C10G 35/04 585/319 |
| 8,822,747 B2 | 9/2014 | Corradi et al. | |
| 9,000,247 B2 | 4/2015 | Abudawoud | |
| 9,249,068 B2* | 2/2016 | Tinger ................. | B01J 19/2445 |
| 9,295,970 B1 | 3/2016 | Tinger et al. | |
| 9,302,953 B2 | 4/2016 | Molinier et al. | |
| 9,469,579 B2 | 10/2016 | Molinier et al. | |
| 2005/0197518 A1 | 9/2005 | Miller et al. | |
| 2006/0178544 A1 | 8/2006 | Murray et al. | |
| 2007/0203376 A1 | 8/2007 | Negiz et al. | |
| 2008/0021253 A1 | 1/2008 | Corma Canos et al. | |
| 2009/0112034 A1 | 4/2009 | Levin | |
| 2012/0024755 A1 | 2/2012 | Beech, Jr. et al. | |
| 2012/0083638 A1 | 4/2012 | Boldingh et al. | |
| 2012/0271071 A1 | 10/2012 | Haizmann et al. | |

(Continued)

FOREIGN PATENT DOCUMENTS

| | | |
|---|---|---|
| CN | 105622306 A | 6/2016 |
| EP | 0816311 A1 | 1/1998 |

(Continued)

OTHER PUBLICATIONS

Alario, et al., "Para-xylene Manufacturing: Catalytic Reactions and Processes," 3 Catalytic Science Series: Zeolites for Cleaner Technologies (2002), 189-207.

Arribas; "The Influence of Zeolite Acidity for the Coupled Hydrogenation and Ring Opening of 1-Methylnaphthalene on Pt/USY Catalysts"; Elsevier, Applied Catalysis A: General 230 (2000) 203-217; 15 pgs.

Commissaris, Scott E.; "UOP Parex Process", Handbook of Petroleum Refining Processes Third Edition, 2004, Chapter 2.6, pp. 2.47-2.53.

Eliche-Quesada, et al.; "Effects of Preparation Method and Sulfur Poisoning on the Hydrogenation and Ring Opening of Tetralin on NiW/Zirconium-Doped Mesoporous Silica Catalysts"; Elsevier, Journal of Catalysis 220 (2003) 457-467; 11 pgs.

(Continued)

*Primary Examiner* — Sharon Pregler
(74) *Attorney, Agent, or Firm* — Bracewell LLP; Constance Gall Rhebergen

(57) ABSTRACT

Embodiments include processes and systems for maximizing the production of benzene and para-xylene from heavy reformate. Embodiments include a C9 dealkylation reactor, a transalkylation reactor, and a C10+ dealkylation reactor. The process and system for producing benzene and para-xylene may be configured to additionally produce alkanes in the presence of hydrogen or olefins in the absence of hydrogen. Embodiments may include an aromatic extraction unit to separate non-aromatics from aromatics.

24 Claims, 6 Drawing Sheets

(56) References Cited

U.S. PATENT DOCUMENTS

| | | |
|---|---|---|
| 2012/0271084 A1 | 10/2012 | Haizmann et al. |
| 2013/0165719 A1 | 6/2013 | Negiz et al. |
| 2013/0261365 A1 | 10/2013 | Wang et al. |
| 2014/0100402 A1 | 4/2014 | Gawlik et al. |
| 2015/0094508 A1 | 4/2015 | Corradi et al. |
| 2015/0166435 A1 | 6/2015 | Serban et al. |
| 2016/0046544 A1 | 2/2016 | Molinier et al. |
| 2016/0101405 A1 | 4/2016 | Tinger et al. |
| 2016/0185686 A1 | 6/2016 | Molinier et al. |
| 2016/0311731 A1 | 10/2016 | Amelse |

FOREIGN PATENT DOCUMENTS

| | | |
|---|---|---|
| WO | 0010944 A1 | 3/2000 |
| WO | 2004056945 A1 | 7/2004 |
| WO | 2007137017 A1 | 11/2007 |
| WO | 2008094255 A1 | 8/2008 |
| WO | 2012006039 A2 | 1/2012 |
| WO | 2013158956 A1 | 10/2013 |

OTHER PUBLICATIONS

International Search Report and the Written Opinion for International Application No. PCT/US2013/037304 dated Jul. 4, 2013; pp. 1-9.

International Search Report and Written Opinion for International Application No. PCT/US2018/012129; International Filing Date Jan. 3, 2018; Report dated Apr. 24, 2018 (pp. 1-14).

International Search Report and Written Opinion for International Application No. PCT/US2018/032874; Report dated Jul. 5, 2018; 13 pgs.

Johnson, James A.; "Aromatics Complexes", Handbook of Petroleum Refining Processes Third Edition, 2004, Chapter 2.1, pp. 2.3-2.11.

Kim, et al.; "Novel Ni2P/Zeolite Catalysts for Naphthalene Hydrocracking to BTX"; Elsevier, Catalysis Communications 45 (2014) 133-138; 6 pgs.

Negiz, Antoine and Stoodt, Thomas J.; "UOP Tatoray Process", Handbook of Petroleum Refining Processes Third Edition, 2004, Chapter 2.7, pp. 2.55-2.63.

Silady, Ptrick J.; "UOP Isomar Process", Handbook of Petroleum Refining Processes Third Edition, 2004, Chapter 2.5, pp. 2.39-2.46.

* cited by examiner

PROCESS AND SYSTEM FOR THE PRODUCTION OF PARA-XYLENE AND BENZENE FROM STREAMS RICH IN C6 TO C12+ AROMATICS

BACKGROUND

Field of the Disclosure

The present disclosure generally relates to the processing of heavy reformate. More specifically, embodiments of the disclosure relate to the production of para-xylene and benzene from heavy reformate.

Description of the Related Art

Petrochemical refiners are facing issues with utilization of heavy reformate streams. Environmental regulations by governments and regions around the world are limiting the amount of aromatics (C6+) content in gasoline fuel. Gasoline refiners and blenders traditionally use C6+ aromatics, which include the C6-8 BTEX components (benzene, toluene, ethylbenzene, and xylenes), to improve octane ratings and anti-knocking attributes of motor fuels.

Although motor fuel use is a major consumer of BTEX components, each of the BTEX products has alternative markets for their use besides motor fuels. Benzene is a widely used precursor for many chemical and solvation processes. Toluene and ethylbenzene are also reactants and precursors in chemical and polymerization processes. The three isomers of xylene ($C_8H_{10}$)—para-xylene, meta-xylene, and ortho-xylene—are all petrochemical feedstocks of value. When mixed xylenes form during catalytic reformation, the less commercially valuable meta-xylene forms in greater amounts than either para- or ortho-xylenes because of thermodynamic equilibrium relationships between the three isomers. Market demand, however, currently favors para-xylene followed distantly by ortho-xylene.

Reformate, the bottoms product from naphtha catalytic reforming, and pyrolysis gasoline (pygas), a byproduct of ethylene cracking, are the usual sources for these compounds. Extracting the valuable BTEX components from reformate and pygas leaves a heavy reformate, which includes mainly C9-12+ alkyl aromatic compounds (pygas may also contain diolefins if not previously separated). Heavy reformate can also form from running these processes at higher severity (that is, temperatures) to produce more hydrogen, alkanes and olefins from naphtha.

Coke formation has been an ongoing problem during the heavy reformate refining process because of its negative effects on liquid yield, catalyst deactivation, and operating period. The heavy reformate may include polycyclic aromatic hydrocarbons and various alkylbenzenes, which tend to form coke during the refining processes. These compounds are typically considered as coke precursors.

SUMMARY

Embodiments in the disclosure provide a method for forming para-xylene and benzene from a heavy reformate. The method includes the step of providing a heavy reformate feed stream. The heavy reformate feed stream includes C6-12+ aromatics. The method includes the step of reacting via dealkylation the heavy reformate feed stream to produce a C9 dealkylation product stream. C9-12+ aromatics of the heavy reformate feed stream are selectively converted into C6-8+ aromatics. The C9 dealkylation product stream includes C6-8+ aromatics. The method includes the step of receiving and splitting the C9 dealkylation product stream to produce a benzene product stream, a toluene product stream, and a C8+ aromatics product stream. The method includes the step of receiving and splitting the C8+ aromatics product stream to produce a C8 aromatics product stream, a C9 aromatics product stream, and a C10+ aromatics product stream. The method includes the step of separating the C8 aromatics product stream to produce a para-xylene stream and an ortho-/meta-xylene stream. The ortho-/meta-xylene stream includes ortho-xylene and meta-xylene. The method includes the step of receiving and reacting via transalkylation the toluene product stream, the C9 aromatics product stream, and the ortho-/meta-xylene stream to produce a benzene, toluene, and xylene (BTX) product stream. The BTX product stream includes benzene, toluene, and mixed xylenes. The method includes the step of receiving and reacting via dealkylation the C10+ aromatics product stream to produce a C6-10 aromatics product stream.

In some embodiments, the receiving and reacting via transalkylation step includes isomerizing ortho-xylene and meta-xylene of the ortho-/meta-xylene stream to produce para-xylene.

In some embodiments, olefins are produced in the reacting via dealkylation step, the receiving and reacting via transalkylation step, or the receiving and reacting via dealkylation step. In some embodiments, the olefins include ethylene and propylene.

In some embodiments, alkanes are produced in the reacting via dealkylation step, the receiving and reacting via transalkylation step, or the receiving and reacting via dealkylation step. In some embodiments, the alkanes include ethane and propane.

In some embodiments, the method further includes the step of providing a makeup hydrogen stream to the reacting via dealkylation step, the receiving and reacting via transalkylation step, or the receiving and reacting via dealkylation step, to promote alkane production.

In some embodiments, the method further includes the step of receiving a light gas produced from the reacting via dealkylation step, the receiving and reacting via transalkylation step, or the receiving and reacting via dealkylation step. The light gas includes ethane, propane, and hydrogen. The method further includes the step of separating the light gas via pressure swing adsorption (PSA) to produce a light gas product stream and a hydrogen product stream. The light gas product stream includes ethane and propane. In some embodiments, the reacting via dealkylation step includes providing the hydrogen product stream to promote alkane production. In some embodiments, the receiving and reacting via transalkylation step includes providing the hydrogen product stream to promote alkane production.

In some embodiments, the receiving and splitting the C9 dealkylation product step includes receiving the BTX product stream or the C6-10 aromatics product stream.

In some embodiments, the method further includes the step of receiving and reacting via disproportionation a portion of the toluene product stream to produce a toluene disproportionation product stream. The toluene disproportionation product stream includes benzene and mixed xylenes. In some embodiments, the receiving and splitting the C9 dealkylation product step includes receiving the toluene disproportionation product stream.

In some embodiments, the method further includes the step of receiving and separating the C9 dealkylation product stream to produce an aromatic product stream and a non-aromatic product stream. The method further includes the step of splitting the aromatic product stream to produce the C8 aromatics product stream, the C9 aromatics product stream, and the C10+ aromatics product stream.

In some embodiments, the receiving and splitting the C9 dealkylation product stream step includes producing a C4− light gas stream and a C5-7 product stream. The C4− light gas stream includes ethane, ethylene, propane, propylene, butane, butylene, or 1,3-butadiene. The C5-7 product stream includes benzene, toluene, and C5-7 non-aromatics. In some embodiments, the method further includes the step of receiving and separating the C5-7 product stream to produce the benzene product stream, the toluene product stream, and a non-aromatic product stream. The non-aromatic product stream includes C5-7 non-aromatics.

Embodiments in the disclosure provide a heavy reformate processing system for forming para-xylene and benzene. The heavy reformate processing system includes a C9 dealkylation reactor, a reformate splitter fluidly coupled downstream of the C9 dealkylation reactor, a xylene splitter fluidly coupled downstream of the reformate splitter, a para-xylene separator fluidly coupled downstream of the xylene splitter, a transalkylation reactor fluidly coupled downstream of the reformate splitter, the xylene splitter, and the para-xylene separator, and a C10+ dealkylation reactor fluidly coupled downstream of the xylene splitter. The C9 dealkylation reactor is operable to receive a heavy reformate feed stream and to produce a C9 dealkylation product stream. The heavy reformate feed stream comprises C6-12+ aromatics. The C9 dealkylation selectively dealkylates C9-12+ aromatics to C6-8+ aromatics. The C9 dealkylation product stream includes C6-8+ aromatics. The reformate splitter is operable to receive the C9 dealkylation product stream and to produce a benzene product stream, a toluene product stream, and a C8+ aromatics product stream. The xylene splitter is operable to receive the C8+ aromatics product stream and to produce a C8 aromatics product stream, a C9 aromatics product stream, and a C10+ aromatics product stream. The para-xylene separator is operable to receive the C8 aromatics product stream and to produce a para-xylene stream and an ortho-/meta-xylene stream. The ortho-/meta-xylene stream includes ortho-xylene and meta-xylene. The transalkylation reactor is operable to receive the toluene product stream, the C9 aromatics product stream, and the ortho-/meta-xylene stream. The transalkylation reactor is operable to produce a BTX product stream. The BTX product stream includes benzene, toluene, and mixed xylenes and is introduced into the reformate splitter. The transalkylation reactor is operable to isomerize ortho-xylene and meta-xylene of the ortho-/meta-xylene stream to produce para-xylene. The C10+ dealkylation reactor is operable to receive the C10+ aromatics product stream and to produce a C6-10 aromatics product stream. The C6-10 aromatics product stream is introduced into the reformate splitter.

In some embodiments, the C9 dealkylation reactor, the transalkylation reactor, and the C10+ dealkylation reactor are operable to produce light gases including ethylene and propylene, in the absence of hydrogen.

In some embodiments, the C9 dealkylation reactor, the transalkylation reactor, and the C10+ dealkylation reactor are operable to produce light gases including ethane and propane, in the presence of hydrogen.

In some embodiments, the heavy reformate processing system further includes a PSA unit. The PSA unit is operable to receive ethane, propane, and hydrogen from the C9 dealkylation reactor, the transalkylation reactor, and the C10+ dealkylation reactor. The PSA unit is operable to produce a light gas product stream and a hydrogen product stream. The light gas product stream includes ethane and propane. In some embodiments, the PSA unit is fluidly coupled upstream of the C9 dealkylation unit and the transalkylation reactor. The hydrogen product stream is passed to the C9 dealkylation unit and the transalkylation reactor.

In some embodiments, the heavy reformate processing system further includes an aromatic extraction unit fluidly coupled downstream of the C9 dealkylation reactor and upstream of the reformate splitter. The aromatic extraction unit is operable to receive the C9 dealkylation product stream and to produce an aromatic product stream and a non-aromatic product stream. The aromatic product stream is introduced into the reformate splitter.

In some embodiments, the reformate splitter is operable to produce a C4− light gas stream and a C5-7 product stream. The C4− light gas stream includes ethane, ethylene, propane, propylene, butane, butylene, or 1,3-butadiene. The C5-7 product stream includes benzene, toluene, and C5-7 non-aromatics. In some embodiments, the heavy reformate processing system further includes an aromatic extraction unit fluidly coupled downstream of the reformate splitter and upstream of the transalkylation reactor. The aromatic extraction unit is operable to receive the C5-7 product stream and to produce the benzene product stream, the toluene product stream, and a non-aromatic product stream. The non-aromatic product stream includes C5-7 non-aromatics. The toluene product stream is introduced into the transalkylation reactor.

BRIEF DESCRIPTION OF THE DRAWINGS

So that the manner in which the previously-recited features, aspects, and advantages of the embodiments of this disclosure as well as others that will become apparent are attained and can be understood in detail, a more particular description of the disclosure briefly summarized previously may be had by reference to the embodiments that are illustrated in the drawings that form a part of this specification. However, it is to be noted that the appended drawings illustrate only certain embodiments of the disclosure and are not to be considered limiting of the disclosure's scope as the disclosure may admit to other equally effective embodiments.

Figure 1:
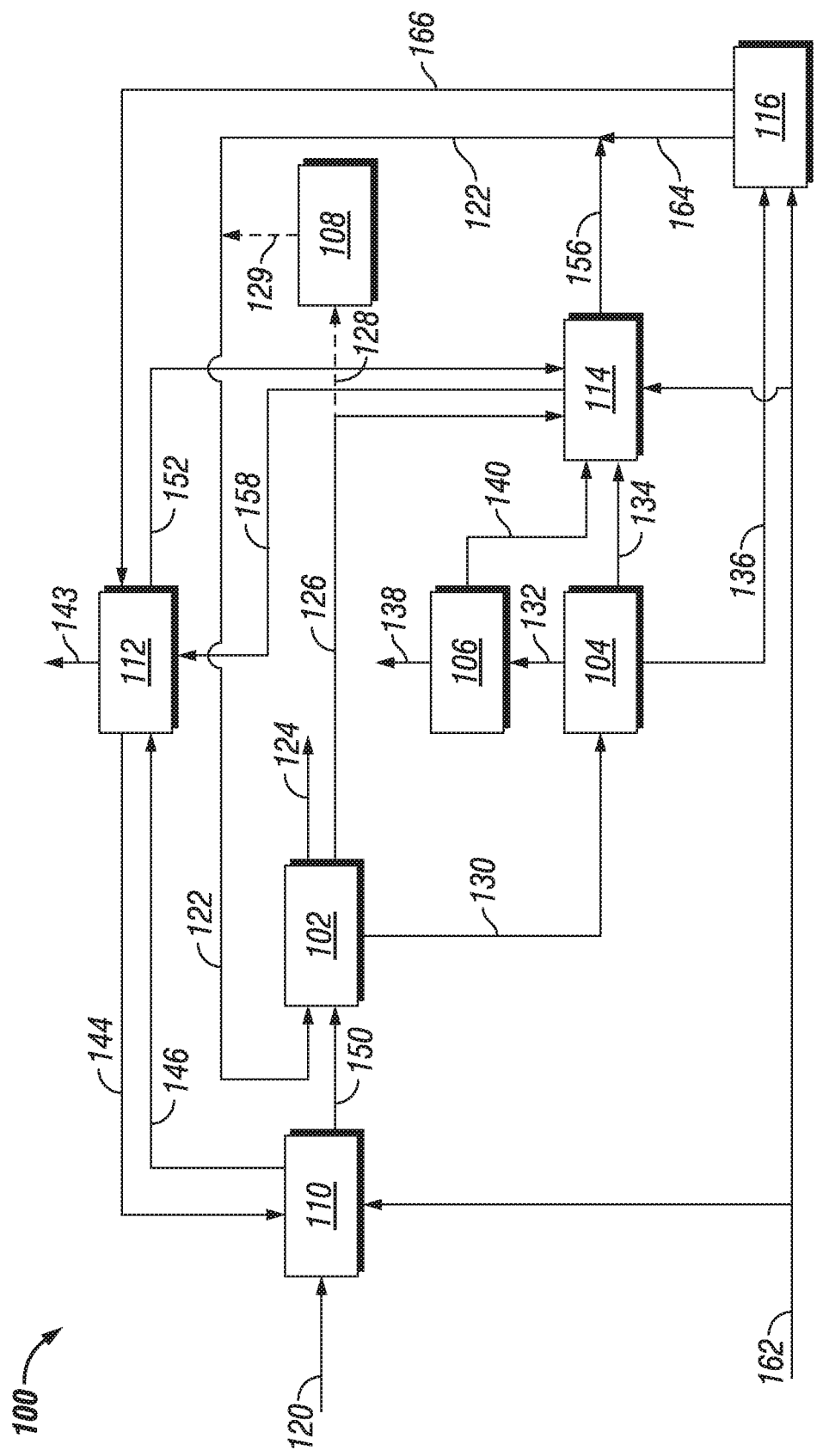
FIG. 1 is a process flow diagram for a dealkylation-transalkylation process for producing benzene and para-xylene from heavy reformate, in accordance with an embodiment of the disclosure.

In the accompanying Figures, similar components or features, or both, may have a similar reference label.

DETAILED DESCRIPTION

The disclosure refers to particular features, including process or method steps. Those of skill in the art understand that the disclosure is not limited to or by the description of embodiments given in the specification. The subject matter of this disclosure is not restricted except only in the spirit of the specification and appended claims.

Those of skill in the art also understand that the terminology used for describing particular embodiments does not limit the scope or breadth of the embodiments of the disclosure. In interpreting the specification and appended claims, all terms should be interpreted in the broadest possible manner consistent with the context of each term. All technical and scientific terms used in the specification and appended claims have the same meaning as commonly understood by one of ordinary skill in the art to which this disclosure belongs unless defined otherwise.

Although the disclosure has been described with respect to certain features, it should be understood that the features and embodiments of the features can be combined with other features and embodiments of those features.

Although the disclosure has been described in detail, it should be understood that various changes, substitutions, and alternations can be made without departing from the principle and scope of the disclosure. Accordingly, the scope of the present disclosure should be determined by the following claims and their appropriate legal equivalents.

As used throughout the disclosure, the singular forms "a," "an," and "the" include plural references unless the context clearly indicates otherwise.

As used throughout the disclosure, the words "comprise," "has," "includes," and all other grammatical variations are each intended to have an open, non-limiting meaning that does not exclude additional elements, components or steps. Embodiments of the present disclosure may suitably "comprise," "consist," or "consist essentially of" the limiting features disclosed, and may be practiced in the absence of a limiting feature not disclosed. For example, it can be recognized by those skilled in the art that certain steps can be combined into a single step.

As used throughout the disclosure, the words "optional" or "optionally" means that the subsequently described event or circumstances can or may not occur. The description includes instances where the event or circumstance occurs and instances where it does not occur.

Where a range of values is provided in the specification or in the appended claims, it is understood that the interval encompasses each intervening value between the upper limit and the lower limit as well as the upper limit and the lower limit. The disclosure encompasses and bounds smaller ranges of the interval subject to any specific exclusion provided. "Substantially free" means less than 1% by the indicated unit of measure. "Significant" means equal to or greater than 10% by the indicated unit of measure. "Detectable" means 0.1% by the indicated unit of measure.

Where reference is made in the specification and appended claims to a method comprising two or more defined steps, the defined steps can be carried out in any order or simultaneously except where the context excludes that possibility.

As used throughout the disclosure, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

As used throughout the disclosure, spatial terms described the relative position of an object or a group of objects relative to another object or group of objects. The spatial relationships apply along vertical and horizontal axes. Orientation and relational words, including "upstream," "downstream" and other like terms, are for descriptive convenience and are not limiting unless otherwise indicated.

As used throughout the disclosure, the term "mixed xylenes" refers to a mixture of all three xylene isomers: para-xylene, ortho-xylene, and meta-xylene.

As used throughout the disclosure, the term "ortho-/meta-xylene" refers to a mixture of the two xylene isomers of ortho-xylene and meta-xylene. The mixture is substantially free (that is, less than 1%) of para-xylene.

As used throughout the disclosure, the term "coke precursors" refers to hydrocarbons that are prone to form coke, which reduces the lifetime of catalysts used in reactors used in the disclosure. For example, polycyclic aromatic hydrocarbons such as naphthalene, anthracene, and phenanthrene, and alkylbenzenes capable of forming polyaromatic hydrocarbons are considered coke precursors.

As used throughout the disclosure, the term "dealkylation" refers to a reaction that results in removing an alkyl group from an aromatic molecule. For example, a trimethylbenzene molecule may undergo dealkylation resulting in a xylene molecule.

As used throughout the disclosure, the term "transalkylation" refers to a reaction that results in an aromatic molecule gaining an alkyl group and another aromatic molecule losing an alkyl group. For example, a toluene molecule and a trimethylbenzene molecule may undergo transalkylation resulting in two xylene molecules.

As used throughout the disclosure, the term "isomerization" refers to a reaction where ortho-/meta-xylene produces mixed xylenes (including para-xylene) by reaching a thermodynamic equilibrium among all three xylene isomers.

As used throughout the disclosure, the term "toluene disproportionation" refers to a reaction where two toluene molecules are converted to a benzene molecule and a xylene molecule.

FIG. 1 shows a process 100 for an embodiment of the dealkylation and transalkylation system for the production of benzene and para-xylene, in accordance with an embodiment of this disclosure. The process 100 includes a C9 dealkylation reactor 110, a reformate splitter 102, a xylene splitter 104, a para-xylene separator 106, a pressure swing adsorption (PSA) unit 112, a transalkylation/isomerization reactor 114 (that is, a reactor that operates to provide both transalkylation and isomerization reactions), and a C10+ dealkylation reactor 116. Optionally, the process can include a toluene disproportionation unit 108. Advantageously, the process 100 does not require a C9/C10+ splitter downstream of the transalkylation/isomerization reactor 114.

A heavy reformate feed stream 120 including C6-12+ aromatics (which can include coke precursors) is introduced into a C9 dealkylation reactor 110. The heavy reformate feed stream 120 can be a stream of reformate from a typical catalytic naphtha reformer. The heavy reformate feed stream 120 can be a stream of pyrolysis gasoline from a steam cracking furnace. The C9 dealkylation reactor 110 receives the heavy reformate feed stream 120 and produces a C9 dealkylation product stream 150. The C9 dealkylation reactor 110 is configured to selectively dealkylate C9-12+ aromatics of the heavy reformate feed stream 120 to C6-8+ aromatics. Also, the C9 dealkylation reactor 110 is configured to selectively crack compounds with two or more aromatic rings, such as naphthalene or derivatives of naphthalene, to produce BTX and light gases. The C9 dealkylation reactor 110 can be optimized to maximize the conversion of C9-12+ aromatics to benzene, toluene, and mixed xylenes. As a result, the C9 dealkylation product stream 150 includes converted C6-8+ aromatics from the dealkylation reaction and unconverted C6-8+ aromatics preexisting in the heavy reformate feed stream 120. Coke precursors are removed by the dealkylation reaction.

In some embodiments, the C9 dealkylation reactor 110 receives a makeup hydrogen stream 162 from an external source. In some embodiments, the C9 dealkylation reactor receives a first hydrogen product stream 144 produced by the PSA unit 112. In some embodiments, the C9 dealkylation reactor 110 produces a first light gas stream 146. The first light gas stream 146 can include light alkanes such as ethane and propane. The first light gas stream 146 can include unreacted hydrogen. In some embodiments, the first light gas stream 146 is introduced into the PSA unit 112.

In some embodiments, the C9 dealkylation reactor 110 may be operated under the following conditions: a temperature in the range of about 200° C. to about 540° C., pressure in the range of about 10 bar to about 50 bar, liquid hourly velocity in the range of about 1 hr$^{-1}$ to about 20 hr$^{-1}$, and a hydrogen to feed stream ratio in the range of about 0 to about 4.

In some embodiments, the catalysts used in the C9 dealkylation reactor 110 for hydrodealkylation with hydrogen may include bifunctional catalysts. The hydrodealkylation catalyst used in the C9 dealkylation reactor 110 may be capable of selectively converting C9-12+ aromatics and hydrogen into toluene, benzene, mixed xylenes, and alkanes. In some embodiments, the hydrodealkylation catalyst may be capable of converting a significant portion or, in some embodiments, all of the C9-12+ aromatics to toluene, benzene, mixed xylenes, and alkanes at the appropriate reaction operating conditions. One skilled in the art may select an appropriate, commercially available hydrodealkylation catalyst for performing the dealkylation portion of the process without undue or excessive experimentation. Such parameters in selecting the physical, selectivity, and activity attributes of an appropriate hydrodealkylation catalyst may include dealkylation stage operating conditions, feed stock compositions, ratios of hydrogen to C9-12+ aromatics, desired conversion efficacy and efficiency, dealkylation stage residence time, and physical attributes of the dealkylation stage. In some embodiments, the catalyst used in the C9 dealkylation reactor 110 may include a fluorinated zeolite catalyst. In some embodiments, the zeolite catalyst may include metal ions (for example, Ni$^{2+}$) incorporated into the crystalline structure of the catalyst. In some embodiments, the metal ions may include other Group 8, Group 9, and Group 10 transition metals, such as cobalt and palladium.

Table 1 shows an example compositional change of aromatics after a C6-12+ aromatics feed passes through the C9 dealkylation reactor 110. As can be seen, the C9 dealkylation reactor 110 substantially reduces less useful C8-12+ aromatics at the outset. The operating conditions and reaction extent of the C9 dealkylation reactor 110 can be varied to maximize C9-12+ aromatics conversion, depending on how many alkyl groups are removed during the dealkylation reaction. The large number of ethyl and, in smaller numbers, propyl groups attached to the aromatics may form light alkanes such as ethane and propane in the presence of hydrogen, and may form light olefins such as ethylene and propylene in the absence of hydrogen.

TABLE 1

| Compound | Conversion (wt. %) |
| --- | --- |
| Ethylbenzene (C8) | >70% |
| Methylethylbenzene (C9) | >95% |
| Trimethylbenzene (C9) | <20% |
| C10 aromatics | >50% |
| C11 aromatics | >50% |
| C12 aromatics | >50% |

The C9 dealkylation product stream 150 is introduced into a reformate splitter 102. The reformate splitter 102 is configured to separate C6 (benzene), C7 (toluene), and C8+ aromatics received from the C9 dealkylation product stream 150. Accordingly, a benzene product stream 124, a toluene product stream 126, and a C8+ aromatics product stream 130 are produced by the reformate splitter 102. The C8+ aromatics product stream 130 includes mixed xylenes. One skilled in the art may select a suitable separation process for extracting benzene and toluene from the C9 dealkylation product stream 150. In some embodiments, benzene can be extracted by solvent extraction. Toluene can be extracted by utilizing a fractionation column.

In some embodiments, the toluene product stream 126 is introduced into the transalkylation/isomerization reactor 114. Optionally, a portion or, in some embodiments, all of the toluene product stream 126 can be introduced into a toluene disproportionation unit 108 via a toluene branch stream 128. The toluene disproportionation unit 108 is configured to convert toluene into about equal stoichiometry of benzene and mixed xylenes. The toluene disproportionation unit 108 produces a toluene disproportionation product stream 129, which is added to a recycled product stream 122. The recycled product stream 122 can be reintroduced into the reformate splitter 102 for further separation. Advantageously, the toluene disproportionation unit 108 can be minimally utilized, or not utilized at all, because all of the toluene produced by the reformate splitter 102 can be directed to the transalkylation/isomerization reactor 114 via the toluene product stream 126. This way, transalkylation efficiency can be substantially improved.

The C8+ aromatics product stream 130 is introduced into a xylene splitter 104. The xylene splitter 104 is configured to separate C8 aromatics (mixed xylenes and ethylbenzene), any remaining C9 aromatics, and any remaining C10+ aromatics received from the C8+ aromatics product stream 130. Accordingly, a C8 aromatics product stream 132, a C9 aromatics product stream 134, and a C10+ aromatics product stream 136 are produced by the xylene splitter 104. One skilled in the art may select a suitable separation process for extracting C8 aromatics and C9 aromatics from the C8+ aromatics product stream 130. For example, C8 aromatics can be recovered from the top, C9 aromatics can be recovered from the side, and C10+ aromatics can be recovered from the bottom of a column. Advantageously, because the C9-12+ aromatics are substantially removed by the C9 dealkylation reactor 110 at the outset, quantities recovered in the C9 aromatics product stream 134 and the C10+ aromatics product stream 136 can be minimal.

The C8 aromatics product stream 132 is introduced into a para-xylene separator 106. The para-xylene separator 106 is configured to separate para-xylene received from the C8 aromatics product stream 132 including mixed xylenes (and ethylbenzene, if any). Accordingly, a para-xylene stream 138 and a ortho-/meta-xylene stream 140 are produced by the para-xylene separator 106. The ortho-/meta-xylene stream 140 includes ortho-xylene and meta-xylene. The ortho-/meta-xylene stream 140 is substantially free of para-xylene. One skilled in the art may select a suitable separation process for extracting para-xylene from the C8 aromatics product stream 132. For example, the para-xylene separator 106 can include an adsorptive process. The para-xylene separator 106 can include a crystallization process.

The C9 aromatics product stream 134 and the ortho-/meta-xylene stream 140 are introduced into the transalkylation/isomerization reactor 114. In some embodiments, the toluene product stream 126 is introduced into the transalkylation/isomerization reactor 114. The transalkylation/isomerization reactor 114 is configured to receive C7-9 aromatics and produce benzene, toluene, mixed xylenes, and light gases. Via transalkylation, the transalkylation/isomerization reactor 114 is configured to convert toluene received from the toluene product stream 126 and C9 aromatics received from the C9 aromatics product stream 134 into mixed xylenes. In some embodiments, the C9 aromatics product stream 134 includes trimethylbenzenes (TMBs). Also via transalkylation, the transalkylation/isomerization reactor 114 is configured to convert toluene received from the toluene product stream 126 into benzene and mixed xylenes. Via isomerization, the transalkylation/isomerization reactor 114 is configured to convert ortho-/meta-xylene received from the ortho-/meta-xylene stream 140 into mixed xylenes by reestablishing the C8 aromatics thermodynamic equilibrium. Accordingly, a BTX product stream 156 is produced by the transalkylation/isomerization reactor 114. Because xylene isomerization is performed in the transalkylation/isomerization reactor 114, a separate transalkylation reactor or a separate isomerization reactor is not required. Advantageously, because the C9-12+ aromatics are substantially removed by the C9 dealkylation reactor 110 at the outset, the transalkylation/isomerization reactor 114 can be of lesser size.

In some embodiments, the transalkylation/isomerization reactor 114 receives a makeup hydrogen stream 162 from an external source. In some embodiments, the transalkylation/isomerization reactor 114 receives a second hydrogen product stream 152 produced by the PSA unit 112. In the presence of hydrogen, the transalkylation/isomerization reactor 114 is configured to dealkylate alkyl groups of the received C7-9 aromatics to produce C6-aromatics (that is, BTX) and light gas. The produced BTX leaves the transalkylation/isomerization reactor 114 via the BTX product stream 156. In some embodiments, the BTX product stream 156 is added to the recycled product stream 122 to be reintroduced into the reformate splitter 102 for further separation. The produced light gas leaves the transalkylation/isomerization reactor 114 via a second light gas stream 158. The second light gas stream 158 can include light alkanes such as ethane and propane. The second light gas stream 158 can include unreacted hydrogen. In some embodiments, the second light gas stream 158 is introduced into the PSA unit 112.

In some embodiments, the transalkylation/isomerization reactor 114 may be operated under the following conditions: a temperature in the range of about 200° C. to about 540° C., pressure in the range of about 10 bar to about 50 bar, liquid hourly velocity in the range of about 1 $hr^{-1}$ to about 20 $hr^{-1}$, and a hydrogen to feed stream ratio in the range of about 0 to about 4.

In some embodiments, the transalkylation catalyst used in the transalkylation/isomerization reactor 114 may be capable of selectively converting TMBs and toluene into mixed xylenes. In some embodiments, the transalkylation catalyst used in the transalkylation/isomerization reactor 114 may be capable of converting a significant portion or, in some embodiments, all of the TMBs in the C9 aromatics product stream 134 to mixed xylenes in the presence of appropriate reaction operating conditions. One skilled in the art may select an appropriate, commercially available transalkylation catalyst for performing the transalkylation portion of the process without undue or excessive experimentation. Such parameters in selecting the physical, selectivity, and activity attributes of an appropriate transalkylation catalyst may include transalkylation operating conditions, feed stock compositions, ratios of toluene to TMBs, desired conversion efficacy and efficiency, stage residence time, and physical attributes of the second stage reaction vessel to support the conversion of TMBs and toluene to mixed xylenes using a transalkylation catalyst. In some embodiments, the catalyst used in the transalkylation/isomerization reactor 114 may include a beta zeolite having an activity promoter selected from the group consisting of silicon, phosphorus, boron, magnesium, tin, titanium, zirconium, molybdenum, germanium, indium, lanthanum, cesium, and any oxide thereof.

The C10+ aromatics product stream 136 is introduced into a C10+ dealkylation reactor 116. The C10+ dealkylation reactor 116 receives the C10+ aromatics product stream 136 and produces a C6-10 aromatics product stream 164. The C10+ dealkylation reactor 116 is configured to selectively dealkylate C10+ aromatics to C6-9 aromatics. Also, the C10+ dealkylation reactor 116 is configured to selectively crack compounds with two or more aromatic rings, such as naphthalene or derivatives of naphthalene, to produce BTX and light gases. The C10+ dealkylation reactor 116 can be optimized to maximize the conversion of C10+ aromatics to BTX. As a result, the C6-10 aromatics product stream 164 includes converted C6-9 aromatics from the dealkylation reaction and unconverted C10 aromatics preexisting in the C10+ aromatics product stream. Advantageously, because the C9-12+ aromatics are substantially removed by the C9 dealkylation reactor 110 at the outset, the C10+ dealkylation reactor 116 can be of lesser size.

In some embodiments, the C10+ dealkylation reactor 116 receives a makeup hydrogen stream 162 from an external source. In the presence of hydrogen, the C10+ dealkylation reactor 116 is configured to convert C10+ aromatics received from the C10+ aromatics product stream 136 into C6-9 aromatics and light gas. The produced light gas leaves the C10+ dealkylation reactor 116 via a third light gas stream 166. The third light gas stream 166 can include light alkanes such as ethane and propane. The third light gas stream 166 can include unreacted hydrogen. In some embodiments, the third light gas stream 166 is introduced into the PSA unit 112. In some embodiments, the C6-10 aromatics product stream 164 is added to the recycled product stream 122 to be reintroduced into the reformate splitter 102 for further separation.

In some embodiments, the C10+ dealkylation reactor 416 may be operated under the following conditions: a temperature in the range of about 200° C. to about 700° C., pressure in the range of about 10 bar to about 50 bar, liquid hourly velocity in the range of about 1 hr$^{-1}$ to about 20 hr$^{-1}$, and a hydrogen to feed stream ratio in the range of about 0 to about 4.

In some embodiments, the C10+ dealkylation reactor 116 may implement a steam dealkylation process and may be operated using steam and a steam dealkylation catalyst under the following conditions and procedure: initially operating at temperature in the range of about 315° C. to about 510° C. for a time period in the range of about 30 to about 180 seconds, during which time the activity of the steam dealkylation catalyst may decrease to less than about 90% of the initial activity as measured by the mole percent conversion of feed aromatics to dealkylate product; interrupting the flow of feed aromatics when the activity of the steam dealkylation catalyst has decreased to less than about 90%; and contacting the steam dealkylation catalyst with steam at a temperature in the range of about 315° C. to about 510° C. to regenerate the catalyst to about 75% of its initial activity and recover the dealkylate product. In some embodiments, the C10+ dealkylation reactor 116 may implement a steam dealkylation process operated at a temperature in the range of about 480° C. to about 550° C.

The hydrodealkylation catalyst used in the C10+ dealkylation reactor 116 may be capable of selectively converting C10+ aromatics (such as methylpropylbenzenes, dimethylethylbenzenes, tetramethylbenzenes, and diethylbenenes) and hydrogen into benzene, toluene, mixed xylenes, and alkanes. In some embodiments, the hydrodealkylation catalyst may be capable of converting a significant portion and, in some embodiments, all of the C10+ aromatics to benzene, toluene, mixed xylenes, and alkanes (for example, ethane and propane) at the appropriate reaction operating conditions. One skilled in the art may select an appropriate, commercially available hydrodealkylation catalyst for performing the dealkylation portion of the process without undue or excessive experimentation. Such parameters in selecting the physical, selectivity, and activity attributes of an appropriate hydrodealkylation catalyst may include dealkylation stage operating conditions, feed stock compositions, ratios of hydrogen to C10+ aromatics, desired conversion efficacy and efficiency, dealkylation stage residence time, and physical attributes of the dealkylation stage. In some embodiments, the catalyst used in the C10+ dealkylation reactor 116 may include a fluorinated zeolite catalyst. In some embodiments, a zeolite catalyst may include metal ions (for example, Ni$^{2+}$) incorporated into the crystalline structure of the catalyst. In some embodiments, the metal ions may include other Group 8, Group 9, and Group 10 transition metals, such as cobalt and palladium.

In some embodiments, the process 100 including the C10+ dealkylation reactor 116 shows an increase in the yield of mixed xylenes over a process without a C10+ dealkylation reactor 116.

The first light gas stream 146, the second light gas stream 158, and the third light gas stream 166 are introduced into the PSA unit 112. Although not shown as a combined stream, the first light gas stream 146, the second light gas stream 158, and the third light gas stream 166 can be combined and fed directly into the PSA unit 112. The PSA unit 112 is configured to recover hydrogen received from the light gases and produce a first hydrogen product stream 144 and a second hydrogen product stream 152 to minimize additional hydrogen requirements. Although not shown as a combined stream, the first hydrogen product stream 144 and the second hydrogen product stream 152 can leave the PSA unit 112 as a single output stream. The first hydrogen product stream 144 is introduced into the C9 dealkylation reactor 110. The second hydrogen product stream 152 is introduced into the transalkylation/isomerization reactor 114. The PSA unit 112 is also configured to produce a light gas product stream 143. The light gas product stream 143 includes a stream of substantially hydrogen-free (that is, less than 1% hydrogen) gases originated from the alkanes produced from the C9 dealkylation reactor 110, the transalkylation/isomerization reactor 114, and the C10+ dealkylation reactor 116. In some embodiments, the light gas product stream 143 can be further processed outside of the process 100, such as being distributed as liquefied petroleum gas (LPG) fuel or being sent to a plant for power generation. The PSA unit 112 can be operated such that the light gas product stream 143 includes no less than about 70 wt. % light alkanes having two to four carbon atoms.

In sum, FIG. 1 shows that the process 100 is configured to produce benzene separated from the reformate splitter 102 as the benzene product stream 124. The process 100 is configured to produce para-xylene separated from the para-xylene separator 106 as the para-xylene stream 138. The process 100 is configured to produce light alkanes separated from the PSA unit 112 as the light gas product stream 143. Advantageously, the C9-12+ aromatics are substantially removed by the C9 dealkylation reactor 110 at the outset, such that the toluene disproportionation unit 108, the transalkylation/isomerization reactor 114, and the C10+ dealkylation reactor 116 can be minimally utilized. Also advantageously, lifetimes of the catalysts used in the C9 dealkylation reactor 110, the transalkylation/isomerization reactor 114, and the C10+ dealkylation reactor 116 are substantially improved due to the removal of coke precursors. Consequently, C6-12+ aromatics can be completely utilized to produce benzene, para-xylene, and light alkanes via the C9 dealkylation process, the transalkylation/isomerization process, and the C10+ dealkylation process.

Figure 2:
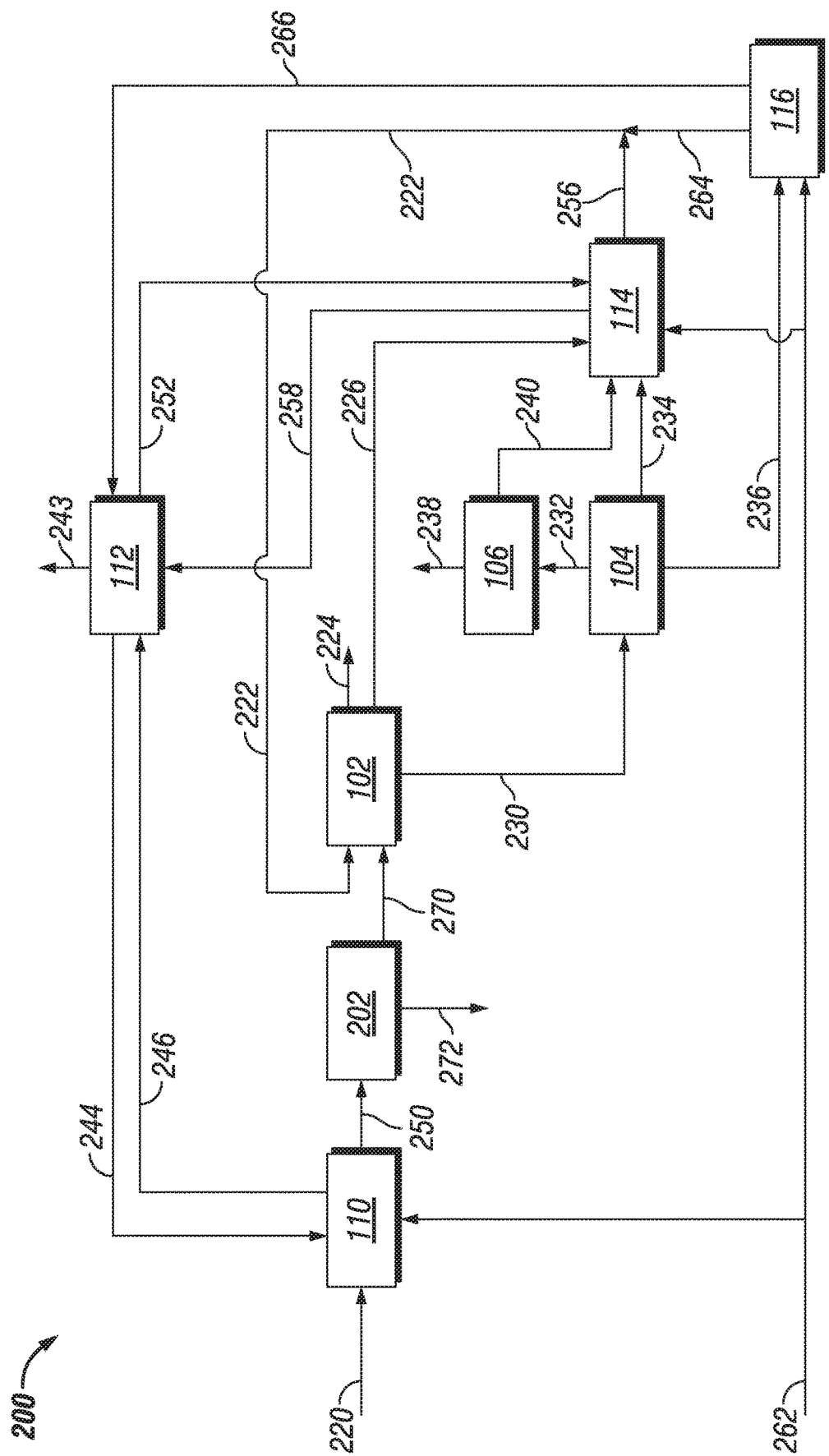
FIG. 2 is a process flow diagram for a dealkylation-transalkylation process for producing benzene and para-xylene from heavy reformate, in accordance with an embodiment of the disclosure.

FIG. 2 shows a process 200 for an embodiment of the dealkylation and transalkylation system for the production of benzene and para-xylene, in accordance with an embodiment of this disclosure. The process 200 includes a C9 dealkylation reactor 110, an aromatic extraction unit 202, a reformate splitter 102, a xylene splitter 104, a para-xylene separator 106, a PSA unit 112, a transalkylation/isomerization reactor 114, and a C10+ dealkylation reactor 116. While the units of FIG. 2 are similar to those of FIG. 1, FIG. 2 shows an embodiment where the aromatic extraction unit is positioned downstream of the C9 dealkylation reactor 110 and upstream of the reformate splitter 102.

A heavy reformate feed stream 220 including C6-C12+ aromatics (which can include coke precursors) is introduced into a C9 dealkylation reactor 110. The heavy reformate feed stream 220 can be a stream of reformate from a typical catalytic naphtha reformer. The heavy reformate feed stream 220 can be a stream of pyrolysis gasoline from a stream cracking furnace. The heavy reformate feed stream 220 can include non-aromatic hydrocarbons, such as naphthenes and paraffins, as well as aromatic hydrocarbons. The C9 dealkylation reactor 110 receives the heavy reformate feed stream 220 and produces a C9 dealkylation product stream 250. The C9 dealkylation reactor 110 is configured to selectively dealkylate C9-C12+ aromatics of the heavy reformate feed stream 220 to C6-C8+ aromatics. Also, the C9 dealkylation reactor 110 is configured to selectively crack compounds with two or more aromatic rings, such as naphthalene or derivatives of naphthalene, to produce BTX and light gases. The C9 dealkylation reactor 110 can be optimized to maximize the conversion of C9-12+ aromatics to benzene, toluene, and mixed xylenes. As a result, the C9 dealkylation product stream 250 includes converted C6-8+ aromatics from the dealkylation reaction and unconverted C6-8+ aromatics preexisting in the heavy reformate feed stream 220. The C9 dealkylation product stream 250 may include non-aromatic hydrocarbons produced as a byproduct of the dealkylation reaction or unreacted non-aromatic hydrocarbons preexisting in the heavy reformate feed stream 220. In any case, coke precursors are removed by the dealkylation reaction.

In some embodiments, the C9 dealkylation reactor 110 receives a makeup hydrogen stream 262 from an external source. In some embodiments, the C9 dealkylation reactor 110 receives a first hydrogen product stream 244 produced by the PSA unit 112. In some embodiments, the C9 dealkylation reactor 110 produces a first light gas stream 246. The first light gas stream 246 can include light alkanes such as ethane and propane. The first light gas stream 246 can include unreacted hydrogen. In some embodiments, the first light gas stream 246 is introduced into the PSA unit 112.

The C9 dealkylation product stream 250 is introduced into an aromatic extraction unit 202. The aromatic extraction unit 202 is configured to separate C6-8+ aromatics and non-aromatic hydrocarbons received from the C9 dealkylation product stream 250. Accordingly, an aromatic product stream 270 and a non-aromatic product stream 272 are produced by the aromatic extraction unit 202. The aromatic product stream 270 includes C6-8+ aromatics. The non-aromatic product stream 272 includes non-aromatic hydrocarbons produced by the C9 dealkylation reactor 110 or unreacted non-aromatic hydrocarbons preexisting in the heavy reformate feed stream 220. The non-aromatic product stream 272 is substantially free (that is, less than 1%) of aromatics. One skilled in the art may select a suitable separation process for extracting aromatics from the aromatic extraction unit 202. For example, chemical extraction or distillation, or a combination of the two, can be used to selectively separate the aromatics from the non-aromatics. In some embodiments, the non-aromatic product stream 272 can be further processed outside of the process 200.

The aromatic product stream 270 is introduced into a reformate splitter 102. The reformate splitter 102 is configured to separate C6 (benzene), C7 (toluene), and C8+ aromatics received from the aromatic product stream 270. Accordingly, a benzene product stream 224, a toluene product stream 226, and a C8+ aromatics product stream 230 are produced by the reformate splitter 102. The C8+ aromatics product stream 230 includes mixed xylenes. One skilled in the art may select a suitable separation process for extracting benzene and toluene from the aromatic product stream 270. In some embodiments, benzene can be extracted by solvent extraction. Toluene can be extracted by utilizing a fractionation column.

The C8+ aromatics product stream 230 is introduced into a xylene splitter 104. The xylene splitter 104 is configured to separate C8 aromatics (mixed xylenes and ethylbenzene), any remaining C9 aromatics, and any remaining C10+ aromatics received from the C8+ aromatics product stream 230. Accordingly, a C8 aromatics product stream 232, a C9 aromatics product stream 234, and a C10+ aromatics product stream 236 are produced by the xylene splitter 104. One skilled in the art may select a suitable separation process for extracting C8 aromatics and C9 aromatics from the C8+ aromatics product stream 230. For example, C8 aromatics can be recovered from the top, C9 aromatics can be recovered from the side, and C10+ aromatics can be recovered from the bottom of a column.

The C8 aromatics product stream 232 is introduced into a para-xylene separator 106. The para-xylene separator 106 is configured to separate para-xylene received from the C8 aromatics product stream 232 including mixed xylenes (and ethylbenzene, if any). Accordingly, a para-xylene stream 238 and a ortho-/meta-xylene stream 240 are produced by the para-xylene separator 106. The ortho-/meta-xylene stream 240 includes ortho-xylene and meta-xylene. The ortho-/meta-xylene stream 240 is substantially free of para-xylene. One skilled in the art may select a suitable separation process for extracting para-xylene from the C8 aromatics product stream 232. For example, the para-xylene separator 106 can include an adsorptive process. The para-xylene separator 106 can include a crystallization process.

The C9 aromatics product stream 234, the ortho-/meta-xylene stream 240, and the toluene product stream 226 are introduced into the transalkylation/isomerization reactor 114. The transalkylation/isomerization reactor 114 is configured to receive C7-9 aromatics and produce benzene, toluene, mixed xylenes, and light gases. Via transalkylation, the transalkylation/isomerization reactor 114 is configured to convert toluene received from the toluene product stream 226 and C9 aromatics received from the C9 aromatics product stream 234 into mixed xylenes. In some embodiments, the C9 aromatics product stream 234 includes TMBs. Also via transalkylation, the transalkylation/isomerization reactor 114 is configured to convert toluene received from the toluene product stream 226 into benzene and mixed xylenes. Via isomerization, the transalkylation/isomerization reactor 114 is configured to convert ortho-/meta-xylene received from the ortho-/meta-xylene stream 240 into mixed xylenes by reestablishing the C8 aromatics thermodynamic equilibrium. Accordingly, a BTX product stream 256 is produced by the transalkylation/isomerization reactor 114. Because xylene isomerization is performed in the transalkylation/isomerization reactor 114, a separate transalkylation reactor or a separate isomerization reactor is not required.

In some embodiments, the transalkylation/isomerization reactor 114 receives a makeup hydrogen stream 262 from an external source. In some embodiments, the transalkylation/isomerization reactor 114 receives a second hydrogen product stream 252 produced by the PSA unit 112. In the presence of hydrogen, the transalkylation/isomerization reactor 114 is configured to dealkylate alkyl groups of the received C7-9 aromatics to produce BTX and light gas. The produced BTX leaves the transalkylation/isomerization reactor 114 via the BTX product stream 256. In some embodiments, the BTX product stream 256 is added to the recycled product stream 222 to be reintroduced into the reformate splitter 102 for further separation. The produced light gas leaves the transalkylation/isomerization reactor 114 via a second light gas stream 258. The second light gas stream 258 can include light alkanes such as ethane and propane. The second light gas stream 258 can include unreacted hydrogen. In some embodiments, the second light gas stream 258 is introduced into the PSA unit 112.

The C10+ aromatics product stream 236 is introduced into a C10+ dealkylation reactor 116. The C10+ dealkylation reactor 116 receives the C10+ aromatics product stream 236 and produces a C6-10 aromatics product stream 264. The C10+ dealkylation reactor 116 is configured to selectively dealkylate C10+ aromatics to C6-9 aromatics. Also, the C10+ dealkylation reactor 116 is configured to selectively crack compounds with two or more aromatic rings, such as naphthalene or derivatives of naphthalene, to produce BTX and light gases. The C10+ dealkylation reactor 116 can be optimized to maximize the conversion of C10+ aromatics to BTX. As a result, the C6-10 aromatics product stream 264 includes converted C6-9 aromatics from the dealkylation reaction and unconverted C10 aromatics preexisting in the C10+ aromatics product stream.

In some embodiments, the C10+ dealkylation reactor 116 receives a makeup hydrogen stream 262 from an external source. In the presence of hydrogen, the C10+ dealkylation reactor 116 is configured to convert C10+ aromatics received from the C10+ aromatics product stream 236 into C6-9 aromatics and light gas. The produced light gas leaves the C10+ dealkylation reactor 116 via a third light gas stream 266. The third light gas stream 266 can include light alkanes such as ethane and propane. The third light gas stream 266 can include unreacted hydrogen. In some embodiments, the third light gas stream 266 is introduced into the PSA unit 112. In some embodiments, the C6-10 aromatics product stream 264 is added to the recycled product stream 222 to be reintroduced into the reformate splitter 102 for further separation.

The first light gas stream 246, the second light gas stream 258, and the third light gas stream 266 are introduced into the PSA unit 112. Although not shown as a combined stream, the first light gas stream 246, the second light gas stream 258, and the third light gas stream 266 can be combined and fed directly into the PSA unit 112. The PSA unit 112 is configured to recover hydrogen received from the light gases and produce a first hydrogen product stream 244 and a second hydrogen product stream 252 to minimize additional hydrogen requirements. Although not shown as a combined stream, the first hydrogen product stream 244 and the second hydrogen product stream 252 can leave the PSA unit 112 as a single output stream. The first hydrogen product stream 244 is introduced into the C9 dealkylation reactor 110. The second hydrogen product stream 252 is introduced into the transalkylation/isomerization reactor 114. The PSA unit 112 is also configured to produce a light gas product stream 243. The light gas product stream 243 includes a stream of hydrogen-free gases originated from the alkanes produced from the C9 dealkylation reactor 110, the transalkylation/isomerization reactor 114, and the C10+ dealkylation reactor 116. In some embodiments, the light gas product stream 243 can be further processed outside of the process 200, such as being distributed as LPG fuel or being sent to a plant for power generation. The PSA unit 112 can be operated such that the light gas product stream 243 includes no less than about 70 wt. % light alkanes having two to four carbon atoms.

Figure 3:
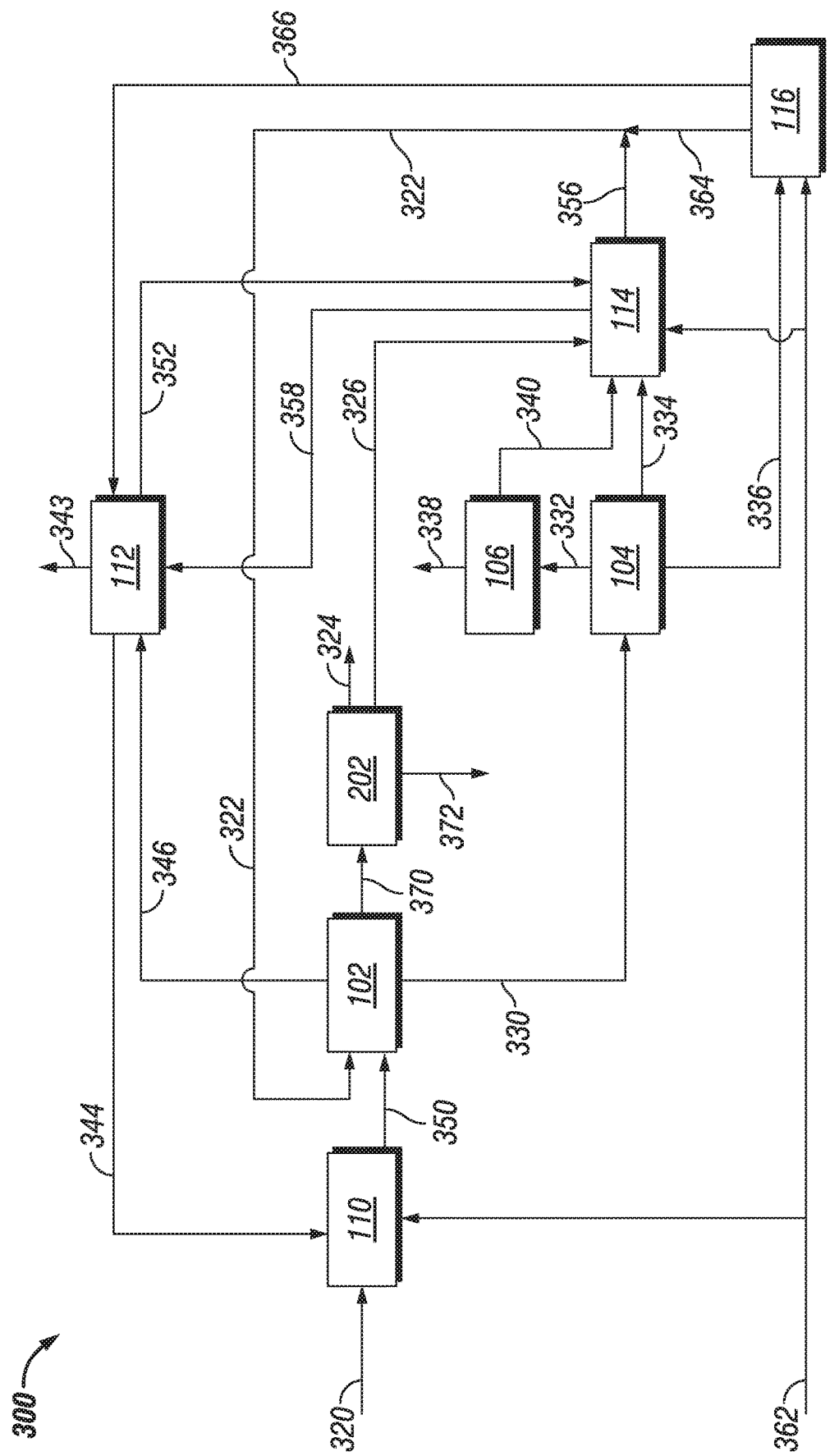
FIG. 3 is a process flow diagram for a dealkylation-transalkylation process for producing benzene and para-xylene from heavy reformate, in accordance with an embodiment of the disclosure.

FIG. 3 shows a process 300 for an embodiment of the dealkylation and transalkylation system for the production of benzene and para-xylene, in accordance with an embodiment of this disclosure. The process 300 includes a C9 dealkylation reactor 110, a reformate splitter 102, an aromatic extraction unit 202, a xylene splitter 104, a para-xylene separator 106, a PSA unit 112, a transalkylation/isomerization reactor 114, and a C10+ dealkylation reactor 116. While the units of FIG. 3 are similar to those of FIG. 1 and FIG. 2, FIG. 3 shows an embodiment where the aromatic extraction unit is positioned downstream of the reformate splitter 102.

A heavy reformate feed stream 320 including C6-C12+ aromatics (which can include coke precursors) is introduced into a C9 dealkylation reactor 110. The heavy reformate feed stream 320 can be a stream of reformate from a typical catalytic naphtha reformer. The heavy reformate feed stream 320 can be a stream of pyrolysis gasoline from a stream cracking furnace. The heavy reformate feed stream 320 can include non-aromatic hydrocarbons, such as naphthenes and paraffins, as well as aromatic hydrocarbons. The C9 dealkylation reactor 110 receives the heavy reformate feed stream 320 and produces a C9 dealkylation product stream 350. The C9 dealkylation reactor 110 is configured to selectively dealkylate C9-C12+ aromatics of the heavy reformate feed stream 320 to C6-C8+ aromatics. Also, the C9 dealkylation reactor 110 is configured to selectively crack compounds with two or more aromatic rings, such as naphthalene or derivatives of naphthalene, to produce BTX and light gases. The C9 dealkylation reactor 110 can be optimized to maximize the conversion of C9-12+ aromatics to benzene, toluene, and mixed xylenes. As a result, the C9 dealkylation product stream 350 includes converted C6-8+ aromatics from the dealkylation reaction and unconverted C6-8+ aromatics preexisting in the heavy reformate feed stream 320. The C9 dealkylation product stream 350 may include non-aromatic hydrocarbons produced as a byproduct of the dealkylation reaction or unreacted non-aromatic hydrocarbons preexisting in the heavy reformate feed stream 320. The C9 dealkylation product stream may include light alkanes such as ethane, propane, butanes, and pentanes produced as a byproduct of the dealkylation reaction. The C9 dealkylation product stream 350 may not include non-aromatic hydrocarbons having more than seven carbon atoms. In any case, coke precursors are removed by the dealkylation reaction.

In some embodiments, the C9 dealkylation reactor 110 receives a makeup hydrogen stream 362 from an external source. In some embodiments, the C9 dealkylation reactor 110 receives a first hydrogen product stream 344 produced by the PSA unit 112.

The C9 dealkylation product stream 350 is introduced into a reformate splitter 102. The reformate splitter 102 is configured to separate C4– hydrocarbons (light alkanes such as ethane, propane, and butanes), C5-7 hydrocarbons (including aromatic and non-aromatic), and C8+ hydrocarbons (substantially aromatic) received from the C9 dealkylation product stream 350. Accordingly, a first light gas stream 346, a C5-7 product stream 370, and a C8+ aromatics product stream 330 are produced by the reformate splitter 102. The C8+ aromatics product stream 330 includes mixed xylenes. The first light gas stream 346 can include light alkanes such as ethane, propane, and butane. The first light gas stream 346 can include unreacted hydrogen from the C9 dealkylation reactor 110. In some embodiments, the first light gas stream 346 is introduced into the PSA unit 112. One skilled in the art may select a suitable separation process for separating C4-, C5-7, and C8+ hydrocarbons from the C9 dealkylation product stream 350. For example, C4– hydrocarbons can be recovered from the top, C5-7 hydrocarbons can be recovered from the side, and C8+ hydrocarbons can be recovered from the bottom of a column.

The C5-7 product stream 370 is introduced into an aromatic extraction unit 202. The aromatic extraction unit 202 is configured to separate benzene, toluene, and C5-7 non-aromatic hydrocarbons received from the C5-7 product stream 370. Accordingly, a benzene product stream 324, a toluene product stream 326, and a non-aromatic product stream 372 are produced by the aromatic extraction unit 202. The non-aromatic product stream 372 includes non-aromatic hydrocarbons produced by the C9 dealkylation reactor 110. The non-aromatic product stream 372 is substantially free of aromatics. One skilled in the art may select a suitable separation process for extracting aromatics from the aromatic extraction unit 202. For example, chemical extraction or distillation, or a combination of the two, can be used to selectively separate the aromatics from the non-aromatics.

One skilled in the art may select a suitable separation process for extracting benzene and toluene from the aromatics separated from the non-aromatics. In some embodiments, benzene can be extracted by solvent extraction. Toluene can be extracted by utilizing a fractionation column. In some embodiments, the non-aromatic product stream 372 can be further processed outside of the process 300.

The C8+ aromatics product stream 330 is introduced into a xylene splitter 104. The xylene splitter 104 is configured to separate C8 aromatics (mixed xylenes and ethylbenzene), any remaining C9 aromatics, and any remaining C10+ aromatics received from the C8+ aromatics product stream 330. Accordingly, a C8 aromatics product stream 332, a C9 aromatics product stream 334, and a C10+ aromatics product stream 336 are produced by the xylene splitter 104. One skilled in the art may select a suitable separation process for extracting C8 aromatics and C9 aromatics from the C8+ aromatics product stream 330. For example, C8 aromatics can be recovered from the top, C9 aromatics can be recovered from the side, and C10+ aromatics can be recovered from the bottom of a column.

The C8 aromatics product stream 332 is introduced into a para-xylene separator 106. The para-xylene separator 106 is configured to separate para-xylene received from the C8 aromatics product stream 332 including mixed xylenes (and ethylbenzene, if any). Accordingly, a para-xylene stream 338 and a ortho-/meta-xylene stream 340 are produced by the para-xylene separator 106. The ortho-/meta-xylene stream 340 includes ortho-xylene and meta-xylene. The ortho-/meta-xylene stream 340 is substantially free of para-xylene. One skilled in the art may select a suitable separation process for extracting para-xylene from the C8 aromatics product stream 332. For example, the para-xylene separator 106 can include an adsorptive process. The para-xylene separator 106 can include a crystallization process.

The C9 aromatics product stream 334, the ortho-/meta-xylene stream 340, and the toluene product stream 326 are introduced into the transalkylation/isomerization reactor 114. The transalkylation/isomerization reactor 114 is configured to receive C7-9 aromatics and produce benzene, toluene, mixed xylenes, and light gases. Via transalkylation, the transalkylation/isomerization reactor 114 is configured to convert toluene received from the toluene product stream 326 and C9 aromatics received from the C9 aromatics product stream 334 into mixed xylenes. In some embodiments, the C9 aromatics product stream 334 includes TMBs. Also via transalkylation, the transalkylation/isomerization reactor 114 is configured to convert toluene received from the toluene product stream 326 into benzene and mixed xylenes. Via isomerization, the transalkylation/isomerization reactor 114 is configured to convert ortho-/meta-xylene received from the ortho-/meta-xylene stream 340 into mixed xylenes by reestablishing the C8 aromatics thermodynamic equilibrium. Accordingly, a BTX product stream 356 is produced by the transalkylation/isomerization reactor 114. Because xylene isomerization is performed in the transalkylation/isomerization reactor 114, a separate transalkylation reactor or a separate isomerization reactor is not required.

In some embodiments, the transalkylation/isomerization reactor 114 receives a makeup hydrogen stream 362 from an external source. In some embodiments, the transalkylation/isomerization reactor 114 receives a second hydrogen product stream 352 produced by the PSA unit 112. In the presence of hydrogen, the transalkylation/isomerization reactor 114 is configured to dealkylate alkyl groups of the received C7-9 aromatics to produce BTX and light gas. The produced BTX leaves the transalkylation/isomerization reactor 114 via the BTX product stream 356. In some embodiments, the BTX product stream 356 is added to the recycled product stream 322 to be reintroduced into the reformate splitter 102 for further separation. The produced light gas leaves the transalkylation/isomerization reactor 114 via a second light gas stream 358. The second light gas stream 358 can include light alkanes such as ethane and propane. The second light gas stream 358 can include unreacted hydrogen. In some embodiments, the second light gas stream 358 is introduced into the PSA unit 112.

The C10+ aromatics product stream 336 is introduced into a C10+ dealkylation reactor 116. The C10+ dealkylation reactor 116 receives the C10+ aromatics product stream 336 and produces a C6-10 aromatics product stream 364. The C10+ dealkylation reactor 116 is configured to selectively dealkylate C10+ aromatics to C6-9 aromatics. Also, the C10+ dealkylation reactor 116 is configured to selectively crack compounds with two or more aromatic rings, such as naphthalene or derivatives of naphthalene, to produce BTX and light gases. The C10+ dealkylation reactor 116 can be optimized to maximize the conversion of C10+ aromatics to BTX. As a result, the C6-10 aromatics product stream 364 includes converted C6-9 aromatics from the dealkylation reaction and unconverted C10 aromatics preexisting in the C10+ aromatics product stream.

In some embodiments, the C10+ dealkylation reactor 116 receives a makeup hydrogen stream 362 from an external source. In the presence of hydrogen, the C10+ dealkylation reactor 116 is configured to convert C10+ aromatics received from the C10+ aromatics product stream 336 into C6-9 aromatics and light gas. The produced light gas leaves the C10+ dealkylation reactor 116 via a third light gas stream 366. The third light gas stream 366 can include light alkanes such as ethane and propane. The third light gas stream 366 can include unreacted hydrogen. In some embodiments, the third light gas stream 366 is introduced into the PSA unit 112. In some embodiments, the C6-10 aromatics product stream 364 is added to the recycled product stream 322 to be reintroduced into the reformate splitter 102 for further separation.

The first light gas stream 346, the second light gas stream 358, and the third light gas stream 366 are introduced into the PSA unit 112. Although not shown as a combined stream, the first light gas stream 346, the second light gas stream 358, and the third light gas stream 366 can be combined and fed directly into the PSA unit 112. The PSA unit 112 is configured to recover hydrogen received from the light gases and produce a first hydrogen product stream 344 and a second hydrogen product stream 352 to minimize additional hydrogen requirements. Although not shown as a combined stream, the first hydrogen product stream 344 and the second hydrogen product stream 352 can leave the PSA unit 112 as a single output stream. The first hydrogen product stream 344 is introduced into the C9 dealkylation reactor 110. The second hydrogen product stream 352 is introduced into the transalkylation/isomerization reactor 114. The PSA unit 112 is also configured to produce a light gas product stream 343. The light gas product stream 343 includes a stream of hydrogen-free gases originated from the alkanes produced from the C9 dealkylation reactor 110, the transalkylation/isomerization reactor 114, and the C10+ dealkylation reactor 116. In some embodiments, the light gas product stream 343 can be further processed outside of the process 300, such as being distributed as LPG fuel or being sent to a plant for power generation. The PSA unit 112 can be operated such that the light gas product stream 343 includes no less than about 70 wt. % light alkanes having two to four carbon atoms.

Figure 4:
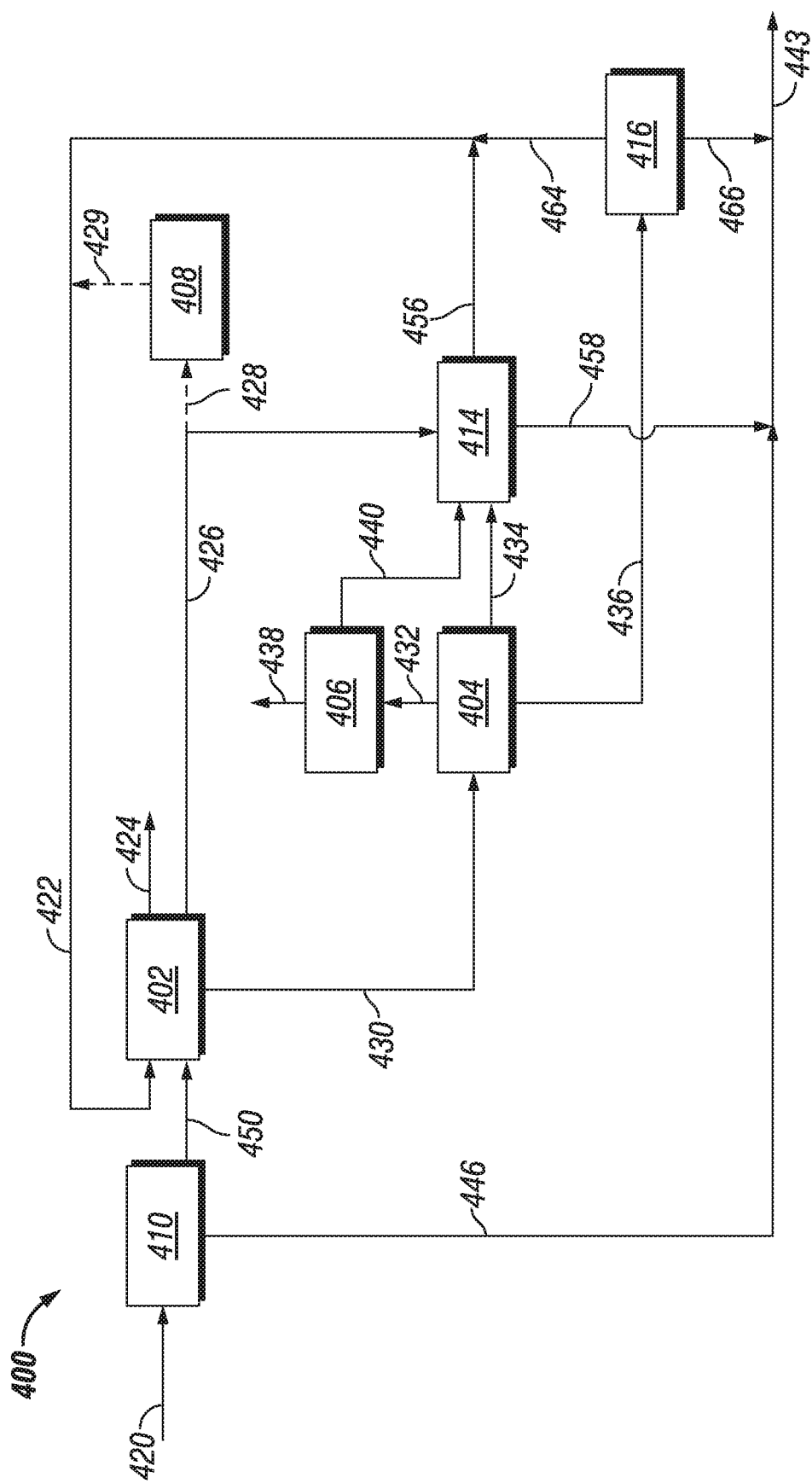
FIG. 4 is a process flow diagram for a dealkylation-transalkylation process for producing benzene and para-xylene from heavy reformate in the absence of hydrogen, in accordance with an embodiment of the disclosure.

FIG. 4 shows a process 400 for an embodiments of the dealkylation and transalkylation system for the production of benzene and para-xylene in the absence of hydrogen, in accordance with an embodiment of this disclosure. The process 400 includes a C9 dealkylation reactor 410, a reformate splitter 402, a xylene splitter 404, a para-xylene separator 406, a transalkylation/isomerization reactor 414, and a C10+ dealkylation reactor 416. Optionally, the process can include a toluene disproportionation unit 408. The process 400 does not include a makeup hydrogen stream. The process 400 does not include a PSA unit. Advantageously, the process 400 does not require a C9/C10+ splitter downstream of the transalkylation/isomerization reactor 414. While the units of FIG. 4 are similar to those of FIG. 1, FIG. 4 shows an embodiment where no hydrogen supply is provided to the process 400.

A heavy reformate feed stream 420 including C6-C12+ aromatics (which can include coke precursors) is introduced into a C9 dealkylation reactor 410. The heavy reformate feed stream 420 can be a stream of reformate from a typical catalytic naphtha reformer. The heavy reformate feed stream 420 can be a stream of pyrolysis gasoline from a steam cracking furnace. The C9 dealkylation reactor 410 receives the heavy reformate feed stream 420 and produces a C9 dealkylation product stream 450. The C9 dealkylation reactor 410 is configured to selectively dealkylate C9-C12+ aromatics of the heavy reformate feed stream 420 to C6-C8+ aromatics. Also, the C9 dealkylation reactor 410 is configured to selectively crack compounds with two or more aromatic rings, such as naphthalene or derivatives of naphthalene, to produce BTX and light gases. The C9 dealkylation reactor 410 can be optimized to maximize the conversion of C9-12+ aromatics to benzene, toluene, and mixed xylenes. As a result, the C9 dealkylation product stream 450 includes converted C6-8+ aromatics from the dealkylation reaction and unconverted C6-8+ aromatics preexisting in the heavy reformate feed stream 420. Coke precursors are removed by the dealkylation reaction.

In some embodiments, the C9 dealkylation reactor 110 produces a first light gas stream 446. The first light gas stream 446 can include light olefins such as ethylene and propylene. In some embodiments, the first light gas stream 446 is combined with a second light gas stream 458 and a third light gas stream 466 to form a light gas product stream 443. In some embodiments, the first light gas stream 446 can be further processed outside of the process 400.

In some embodiments, the C9 dealkylation reactor 410 may be operated under the following conditions: a temperature in the range of about 200° C. to about 540° C., pressure in the range of about 10 bar to about 50 bar, and a liquid hourly velocity in the range of about 1 hr$^{-1}$ to about 20 hr$^{-1}$.

In some embodiments, the configuration and catalyst formulation of the C9 dealkylation reactor 410 can be different than that of the C9 dealkylation reactor 110 (shown in FIGS. 1-3) when the C9-12+ aromatics are processed in the absence of hydrogen. In some embodiments, the catalysts used in the C9 dealkylation reactor 410 in the absence of hydrogen may include monofunctional catalysts. Such monofunctional catalysts may include dealkylation catalysts without a metal component in the catalyst formulation. The dealkylation catalyst used in the C9 dealkylation reactor 410 may be capable of selectively converting C9-12+ aromatics into toluene, benzene, mixed xylenes, and olefins. In some embodiments, the dealkylation catalyst may be capable of converting a significant portion and, in some embodiments, all of the C9-12+ aromatics to toluene, benzene, mixed xylenes, and olefins at the appropriate reaction operating conditions. One skilled in the art may select an appropriate, commercially available dealkylation catalyst for performing the dealkylation portion of the process without undue or excessive experimentation. Such parameters in selecting the physical, selectivity, and activity attributes of an appropriate dealkylation catalyst may include dealkylation stage operating conditions, feed stock compositions, desired conversion efficacy and efficiency, dealkylation stage residence time, and physical attributes of the dealkylation stage. In some embodiments, the catalyst used in the C9 dealkylation reactor 410 may include a fluorinated zeolite catalyst. In some embodiments, the C9 dealkylation reactor 410 operated to produce olefins in the absence of hydrogen may be a fluid-bed reactor or a moving bed-reactor.

The C9 dealkylation product stream 450 is introduced into a reformate splitter 402. The reformate splitter 402 is configured to separate C6 (benzene), C7 (toluene), and C8+ aromatics received from the C9 dealkylation product stream 450. Accordingly, a benzene product stream 424, a toluene product stream 426, and a C8+ aromatics product stream 430 are produced by the reformate splitter 402. The C8+ aromatics product stream 430 includes mixed xylenes. One skilled in the art may select a suitable separation process for extracting benzene and toluene from the C9 dealkylation product stream 450. In some embodiments, benzene can be extracted by solvent extraction. Toluene can be extracted by utilizing a fractionation column.

In some embodiments, the toluene product stream 426 is introduced into the transalkylation/isomerization reactor 414. Optionally, a portion or, in some embodiments, all of the toluene product stream 426 can be introduced into a toluene disproportionation unit 408 via a toluene branch stream 428. The toluene disproportionation unit 408 is configured to convert toluene into about equal stoichiometry of benzene and mixed xylenes. The toluene disproportionation unit 408 produces a toluene disproportionation product stream 429, which is added to a recycled product stream 422. The recycled product stream 422 can be reintroduced into the reformate splitter 402 for further separation. Advantageously, the toluene disproportionation unit 408 can be minimally utilized, or not utilized at all, because all of the toluene produced by the reformate splitter 402 can be directed to the transalkylation/isomerization reactor 414 via the toluene product stream 426. This way, transalkylation efficiency can be substantially improved.

The C8+ aromatics product stream 430 is introduced into a xylene splitter 404. The xylene splitter 404 is configured to separate C8 aromatics (mixed xylenes and ethylbenzene), any remaining C9 aromatics, and any remaining C10+ aromatics received from the C8+ aromatics product stream 430. Accordingly, a C8 aromatics product stream 432, a C9 aromatics product stream 434, and a C10+ aromatics product stream 436 are produced by the xylene splitter 404. One skilled in the art may select a suitable separation process for extracting C8 aromatics and C9 aromatics from the C8+ aromatics product stream 430. For example, C8 aromatics can be recovered from the top, C9 aromatics can be recovered from the side, and C10+ aromatics can be recovered from the bottom of a column. Advantageously, because the C9-12+ aromatics are substantially removed by the C9 dealkylation reactor 410 at the outset, quantities recovered in the C9 aromatics product stream 434 and the C10+ aromatics product stream 436 can be minimal.

The C8 aromatics product stream 432 is introduced into a para-xylene separator 406. The para-xylene separator 406 is configured to separate para-xylene received from the C8 aromatics product stream 432 including mixed xylenes (and ethylbenzene, if any). Accordingly, a para-xylene stream 438 and a ortho-/meta-xylene stream 440 are produced by the para-xylene separator 406. The ortho-/meta-xylene stream 440 includes ortho-xylene and meta-xylene. The ortho-/meta-xylene stream 440 is substantially free of para-xylene. One skilled in the art may select a suitable separation process for extracting para-xylene from the C8 aromatics product stream 432. For example, the para-xylene separator 406 can include an adsorptive process. The para-xylene separator 406 can include a crystallization process.

The C9 aromatics product stream 434 and the ortho-/meta-xylene stream 440 are introduced into the transalkylation/isomerization reactor 414. In some embodiments, the toluene product stream 426 is introduced into the transalkylation/isomerization reactor 414. The transalkylation/isomerization reactor 414 is configured to receive C7-9 aromatics and produce benzene, toluene, mixed xylenes, and light gases. Via transalkylation, the transalkylation/isomerization reactor 414 is configured to convert toluene received from the toluene product stream 426 and C9 aromatics received from the C9 aromatics product stream 434 into mixed xylenes. In some embodiments, the C9 aromatics product stream 434 includes TMBs. Also via transalkylation, the transalkylation/isomerization reactor 414 is configured to convert toluene received from the toluene product stream 426 into benzene and mixed xylenes. Via isomerization, the transalkylation/isomerization reactor 414 is configured to convert ortho-/meta-xylene received from the ortho-/meta-xylene stream 440 into mixed xylenes by reestablishing the C8 aromatics thermodynamic equilibrium. Accordingly, a BTX product stream 456 is produced by the transalkylation/isomerization reactor 414. Because xylene isomerization is performed in the transalkylation/isomerization reactor 414, a separate transalkylation reactor or a separate isomerization reactor is not required. Advantageously, because the C9-12+ aromatics are substantially removed by the C9 dealkylation reactor 410 at the outset, the transalkylation/isomerization reactor 414 can be of lesser size.

In some embodiments, in the absence of hydrogen, the transalkylation/isomerization reactor 414 is configured to dealkylate alkyl groups of the received C7-9 aromatics to produce BTX and light gas. The produced BTX leaves the transalkylation/isomerization reactor 414 via the BTX product stream 456. In some embodiments, the BTX product stream 456 is added to the recycled product stream 422 to be reintroduced into the reformate splitter 402 for further separation. The produced light gas leaves the transalkylation/isomerization reactor 414 via a second light gas stream 458. The second light gas stream 458 can include light olefins such as ethylene and propylene. In some embodiments, the second light gas stream 458 is combined with the first light gas stream 446 and the third light gas stream 466 to form a light gas product stream 443. In some embodiments, the second light gas stream 458 can be further processed outside of the process 400.

In some embodiments, the transalkylation/isomerization reactor 414 may be operated under the following conditions: a temperature in the range of about 200° C. to about 540° C., pressure in the range of about 10 bar to about 50 bar, and liquid hourly velocity in the range of about 1 $hr^{-1}$ to about 20 $hr^{-1}$.

In some embodiments, the transalkylation catalyst used in the transalkylation/isomerization reactor 414 may be capable of selectively converting TMBs and toluene into mixed xylenes. In some embodiments, the transalkylation catalyst used in the transalkylation/isomerization reactor 414 may be capable of converting a significant portion or, in some embodiments, all of the TMBs in the C9 aromatics product stream 434 to mixed xylenes in the presence of appropriate reaction operating conditions. One skilled in the art may select an appropriate, commercially available transalkylation catalyst for performing the transalkylation portion of the process without undue or excessive experimentation. Such parameters in selecting the physical, selectivity, and activity attributes of an appropriate transalkylation catalyst may include transalkylation operating conditions, feed stock compositions, ratios of toluene to TMBs, desired conversion efficacy and efficiency, stage residence time, and physical attributes of the second stage reaction vessel to support the conversion of TMBs and toluene to mixed xylenes using a transalkylation catalyst. In some embodiments, the catalyst used in the transalkylation/isomerization reactor 414 may include a beta zeolite having an activity promoter selected from the group consisting of silicon, phosphorus, boron, magnesium, tin, titanium, zirconium, molybdenum, germanium, indium, lanthanum, cesium, and any oxide thereof.

The C10+ aromatics product stream 436 is introduced into a C10+ dealkylation reactor 416. The C10+ dealkylation reactor 416 receives the C10+ aromatics product stream 436 and produces a C6-10 aromatics product stream 464. The C10+ dealkylation reactor 416 is configured to selectively dealkylate C10+ aromatics to C6-9 aromatics. Also, the C10+ dealkylation reactor 416 is configured to selectively crack compounds with two or more aromatic rings, such as naphthalene or derivatives of naphthalene, to produce BTX and light gases. Additionally, ethyl and propyl groups attached to the C10+ aromatics can form olefins such as ethylene and propylene. The C10+ dealkylation reactor 416 can be optimized to maximize the conversion of C10+ aromatics to BTX. As a result, the C6-10 aromatics product stream 464 includes converted C6-9 aromatics from the dealkylation reaction and unconverted C10 aromatics pre-existing in the C10+ aromatics product stream. Advantageously, because the C9-12+ aromatics are substantially removed by the C9 dealkylation reactor 410 at the outset, the C10+ dealkylation reactor 416 can be of lesser size.

In some embodiments, in the absence of hydrogen, the C10+ dealkylation reactor 416 is configured to convert C10+ aromatics received from the C10+ aromatics product stream 436 into C6-9 aromatics and light gas. The produced light gas leaves the C10+ dealkylation reactor 416 via a third light gas stream 466. The third light gas stream 466 can include light olefins such as ethylene and propylene. In some embodiments, the third light gas stream 466 is combined with the first light gas stream 446 and the second light gas stream 458 to form a light gas product stream 443. In some embodiments, the third light gas stream 466 can be further processed outside of the process 400. In some embodiments, the C6-10 aromatics product stream 464 is added to the recycled product stream 422 to be reintroduced into the reformate splitter 402 for further separation.

In some embodiments, the C10+ dealkylation reactor 416 may be operated under the following conditions: a temperature in the range of about 200° C. to about 700° C., pressure in the range of about 10 bar to about 50 bar, liquid hourly velocity in the range of about 1 $hr^{-1}$ to about 20 $hr^{-1}$, and a hydrogen to feed stream ratio in the range of about 0 to about 4.

In some embodiments, the catalysts used in the C10+ dealkylation reactor 416 in the absence of hydrogen may include monofunctional catalysts. Such monofunctional catalysts may include dealkylation catalysts without a metal component in the catalyst formulation. The hydrodealkylation catalyst used in the C10+ dealkylation reactor 416 may be capable of selectively converting C10+ aromatics (such as methylpropylbenzenes, dimethylethylbenzenes, tetramethylbenzenes, and diethylbenenes) into benzene, toluene, and mixed xylenes. Additionally, the large number of ethyl and, in smaller numbers, propyl groups attached to the C10+ aromatic molecules may easily form olefins such as ethylene and propylene when the dealkylation reaction is performed in the absence of hydrogen. However, rapid catalyst deactivation may occur when the C10+ dealkylation reactor 416 is operated in the absence of hydrogen. In such embodiments, steam may be introduced to the C10+ dealkylation reactor 416, and the C10+ dealkylation reactor 416 may be configured as a fluid-bed or moving-bed catalytic reactor.

In some embodiments, the dealkylation catalyst may be capable of converting a significant portion and, in some embodiments, all of the C10+ aromatics to benzene, toluene, mixed xylenes, and olefins at the appropriate reaction operating conditions. One skilled in the art may select an appropriate, commercially available dealkylation catalyst for performing the dealkylation portion of the process without undue or excessive experimentation. Such parameters in selecting the physical, selectivity, and activity attributes of an appropriate dealkylation catalyst may include dealkylation stage operating conditions, feed stock compositions, desired conversion efficacy and efficiency, dealkylation stage residence time, and physical attributes of the dealkylation stage. In some embodiments, the catalyst used in the C10+ dealkylation reactor 416 may include a fluorinated zeolite catalyst. In such embodiments, the zeolite catalyst may not include any metal ions.

In sum, FIG. 4 shows that the process 400 is configured to produce benzene separated from the reformate splitter 402 as the benzene product stream 424. The process 400 is configured to produce para-xylene separated from the para-xylene separator 406 as the para-xylene stream 438. The process 400 is configured to produce light olefins as the light gas product stream 443. Advantageously, the C9-12+ aromatics are substantially removed by the C9 dealkylation reactor 410 at the outset, such that the toluene disproportionation unit 408, the transalkylation/isomerization reactor 414, and the C10+ dealkylation reactor 416 can be minimally utilized. Also advantageously, lifetimes of the catalysts used in the C9 dealkylation reactor 410, the transalkylation/isomerization reactor 414, and the C10+ dealkylation reactor 416 are substantially improved due to the removal of coke precursors. Consequently, C6-12+ aromatics can be completely utilized to produce benzene, para-xylene, and light olefins via the C9 dealkylation process, the transalkylation/isomerization process, and the C10+ dealkylation process.

Figure 5:
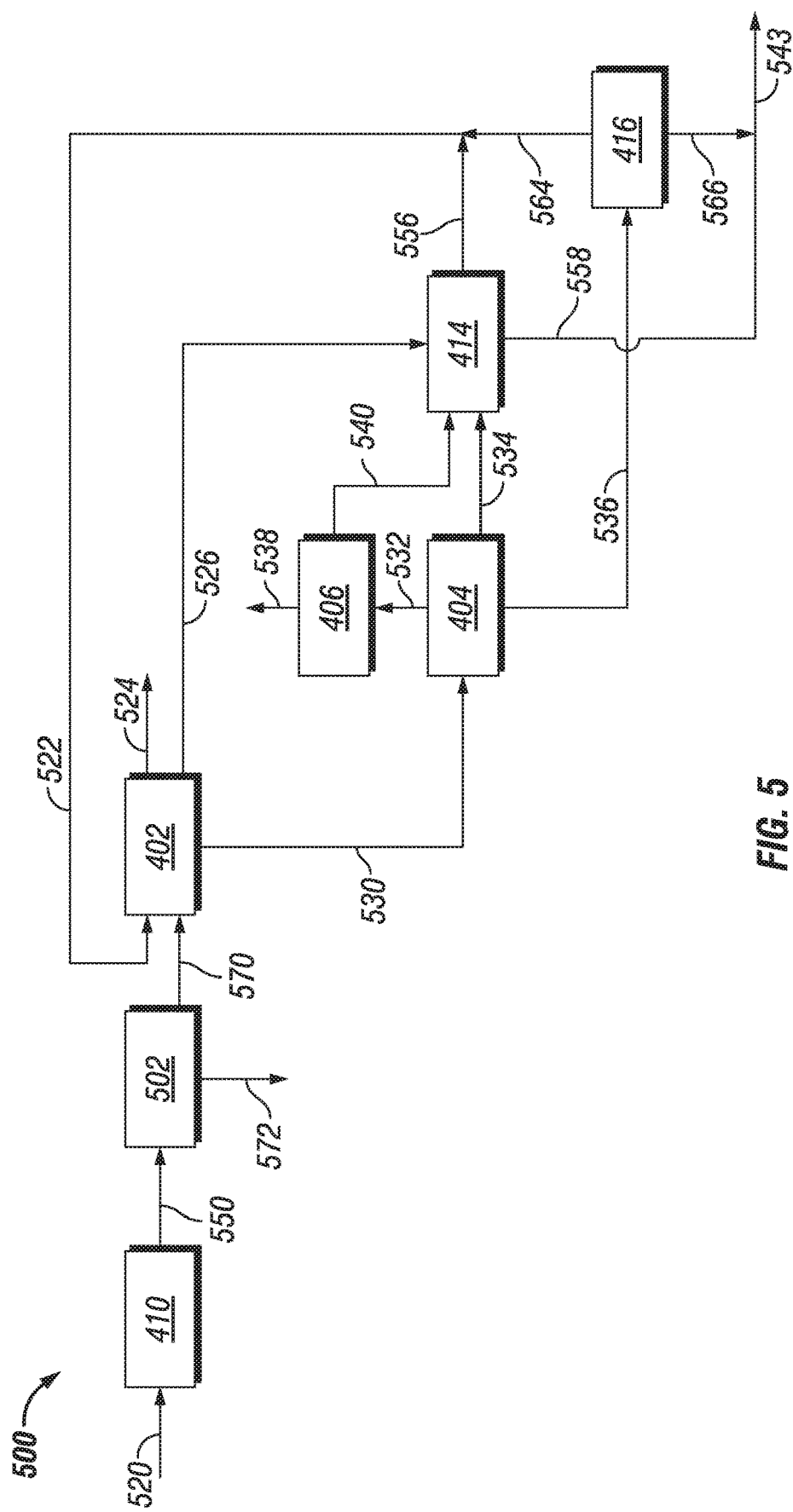
FIG. 5 is a process flow diagram for a dealkylation-transalkylation process for producing benzene and para-xylene from heavy reformate in the absence of hydrogen, in accordance with an embodiment of the disclosure.

FIG. 5 shows a process 500 for an embodiment of the dealkylation and transalkylation system for the production of benzene and para-xylene in the absence of hydrogen, in accordance with an embodiment of this disclosure. The process 500 includes a C9 dealkylation reactor 410, an aromatic extraction unit 502, a reformate splitter 402, a xylene splitter 404, a para-xylene separator 406, a transalkylation/isomerization reactor 414, and a C10+ dealkylation reactor 416. While the units of FIG. 5 are similar to those of FIG. 2 and FIG. 4, FIG. 5 shows an embodiment where the aromatic extraction unit 502 is positioned downstream of the C9 dealkylation reactor 410 and upstream of the reformate splitter 402, and where no hydrogen supply is provided to the process 500.

A heavy reformate feed stream 520 including C6-C12+ aromatics (which can include coke precursors) is introduced into a C9 dealkylation reactor 410. The heavy reformate feed stream 520 can be a stream of reformate from a typical catalytic naphtha reformer. The heavy reformate feed stream 520 can be a stream of pyrolysis gasoline from a stream cracking furnace. The heavy reformate feed stream 520 can include non-aromatic hydrocarbons, such as naphthenes and paraffins, as well as aromatic hydrocarbons. The C9 dealkylation reactor 410 receives the heavy reformate feed stream 520 and produces a C9 dealkylation product stream 550. The C9 dealkylation reactor 410 is configured to selectively dealkylate C9-C12+ aromatics of the heavy reformate feed stream 520 to C6-C8+ aromatics. Also, the C9 dealkylation reactor 410 is configured to selectively crack compounds with two or more aromatic rings, such as naphthalene or derivatives of naphthalene, to produce BTX and light gases. The C9 dealkylation reactor 410 can be optimized to maximize the conversion of C9-12+ aromatics to benzene, toluene, and mixed xylenes. As a result, the C9 dealkylation product stream 550 includes converted C6-8+ aromatics from the dealkylation reaction and unconverted C6-8+ aromatics preexisting in the heavy reformate feed stream 520. The C9 dealkylation product stream 550 may include non-aromatic hydrocarbons, including light olefins such as ethylene and propylene, produced as a byproduct of the dealkylation reaction or unreacted non-aromatic hydrocarbons preexisting in the heavy reformate feed stream 520. In any case, coke precursors are removed by the dealkylation reaction.

The C9 dealkylation product stream 550 is introduced into an aromatic extraction unit 502. The aromatic extraction unit 502 is configured to separate C6-8+ aromatics and non-aromatic hydrocarbons, including light olefins such as ethylene and propylene, received from the C9 dealkylation product stream 550. Accordingly, an aromatic product stream 570 and a non-aromatic product stream 572 are produced by the aromatic extraction unit 502. The aromatic product stream 570 includes C6-8+ aromatics. The non-aromatic product stream 572 includes non-aromatic hydrocarbons, including light olefins such as ethylene and propylene, produced by the C9 dealkylation reactor 410 or unreacted non-aromatic hydrocarbons preexisting in the heavy reformate feed stream 520. The non-aromatic product stream 572 is substantially free of aromatics. One skilled in the art may select a suitable separation process for extracting aromatics from the aromatic extraction unit 502. For example, chemical extraction or distillation, or a combination of the two, can be used to selectively separate the aromatics from the non-aromatics. In some embodiments, the non-aromatic product stream 572 can be further processed outside of the process 500.

The aromatic product stream 570 is introduced into a reformate splitter 402. The reformate splitter 402 is configured to separate C6 (benzene), C7 (toluene), and C8+ aromatics received from the aromatic product stream 570. Accordingly, a benzene product stream 524, a toluene product stream 526, and a C8+ aromatics product stream 530 are produced by the reformate splitter 402. The C8+ aromatics product stream 530 includes mixed xylenes. One skilled in the art may select a suitable separation process for extracting benzene and toluene from the aromatic product stream 570.

In some embodiments, benzene can be extracted by solvent extraction. Toluene can be extracted by utilizing a fractionation column.

The C8+ aromatics product stream 530 is introduced into a xylene splitter 404. The xylene splitter 404 is configured to separate C8 aromatics (mixed xylenes and ethylbenzene), any remaining C9 aromatics, and any remaining C10+ aromatics received from the C8+ aromatics product stream 530. Accordingly, a C8 aromatics product stream 532, a C9 aromatics product stream 534, and a C10+ aromatics product stream 536 are produced by the xylene splitter 404. One skilled in the art may select a suitable separation process for extracting C8 aromatics and C9 aromatics from the C8+ aromatics product stream 530. For example, C8 aromatics can be recovered from the top, C9 aromatics can be recovered from the side, and C10+ aromatics can be recovered from the bottom of a column.

The C8 aromatics product stream 532 is introduced into a para-xylene separator 406. The para-xylene separator 406 is configured to separate para-xylene received from the C8 aromatics product stream 532 including mixed xylenes (and ethylbenzene, if any). Accordingly, a para-xylene stream 538 and a ortho-/meta-xylene stream 540 are produced by the para-xylene separator 406. The ortho-/meta-xylene stream 540 includes ortho-xylene and meta-xylene. The ortho-/meta-xylene stream 540 is substantially free of para-xylene. One skilled in the art may select a suitable separation process for extracting para-xylene from the C8 aromatics product stream 532. For example, the para-xylene separator 406 can include an adsorptive process. The para-xylene separator 406 can include a crystallization process.

The C9 aromatics product stream 534, the ortho-/meta-xylene stream 540, and the toluene product stream 526 are introduced into the transalkylation/isomerization reactor 414. The transalkylation/isomerization reactor 414 is configured to receive C7-9 aromatics and produce benzene, toluene, mixed xylenes, and light gases. Via transalkylation, the transalkylation/isomerization reactor 414 is configured to convert toluene received from the toluene product stream 526 and C9 aromatics received from the C9 aromatics product stream 534 into mixed xylenes. In some embodiments, the C9 aromatics product stream 534 includes TMBs. Also via transalkylation, the transalkylation/isomerization reactor 414 is configured to convert toluene received from the toluene product stream 526 into benzene and mixed xylenes. Via isomerization, the transalkylation/isomerization reactor 414 is configured to convert ortho-/meta-xylene received from the ortho-/meta-xylene stream 540 into mixed xylenes by reestablishing the C8 aromatics thermodynamic equilibrium. Accordingly, a BTX product stream 556 is produced by the transalkylation/isomerization reactor 414. Because xylene isomerization is performed in the transalkylation/isomerization reactor 414, a separate transalkylation reactor or a separate isomerization reactor is not required.

In some embodiments, in the absence of hydrogen, the transalkylation/isomerization reactor 414 is configured to dealkylate alkyl groups of the received C7-9 aromatics to produce BTX and light gas. The produced BTX leaves the transalkylation/isomerization reactor 414 via the BTX product stream 556. In some embodiments, the BTX product stream 556 is added to the recycled product stream 522 to be reintroduced into the reformate splitter 402 for further separation. The produced light gas leaves the transalkylation/isomerization reactor 414 via a first light gas stream 558. The first light gas stream 558 can include light olefins such as ethylene and propylene. In some embodiments, the first light gas stream 558 is combined with a second light gas stream 566 to form a light gas product stream 543. In some embodiments, the first light gas stream 558 can be further processed outside of the process 500.

The C10+ aromatics product stream 536 is introduced into a C10+ dealkylation reactor 416. The C10+ dealkylation reactor 416 receives the C10+ aromatics product stream 536 and produces a C6-10 aromatics product stream 564. The C10+ dealkylation reactor 416 is configured to selectively dealkylate C10+ aromatics to C6-9 aromatics. Also, the C10+ dealkylation reactor 416 is configured to selectively crack compounds with two or more aromatic rings, such as naphthalene or derivatives of naphthalene, to produce BTX and light gases. Additionally, ethyl and propyl groups attached to the C10+ aromatics can form olefins such as ethylene and propylene. The C10+ dealkylation reactor 416 can be optimized to maximize the conversion of C10+ aromatics to BTX. As a result, the C6-10 aromatics product stream 564 includes converted C6-9 aromatics from the dealkylation reaction and unconverted C10 aromatics pre-existing in the C10+ aromatics product stream.

In some embodiments, in the absence of hydrogen, the C10+ dealkylation reactor 416 is configured to convert C10+ aromatics received from the C10+ aromatics product stream 536 into C6-9 aromatics and light gas. The produced light gas leaves the C10+ dealkylation reactor 416 via a second light gas stream 566. The second light gas stream 566 can include light olefins such as ethylene and propylene. In some embodiments, the second light gas stream 566 is combined with the first light gas stream 558 to form a light gas product stream 543. In some embodiments, the second light gas stream 566 can be further processed outside of the process 500. In some embodiments, the C6-10 aromatics product stream 564 is added to the recycled product stream 522 to be reintroduced into the reformate splitter 402 for further separation.

Figure 6:
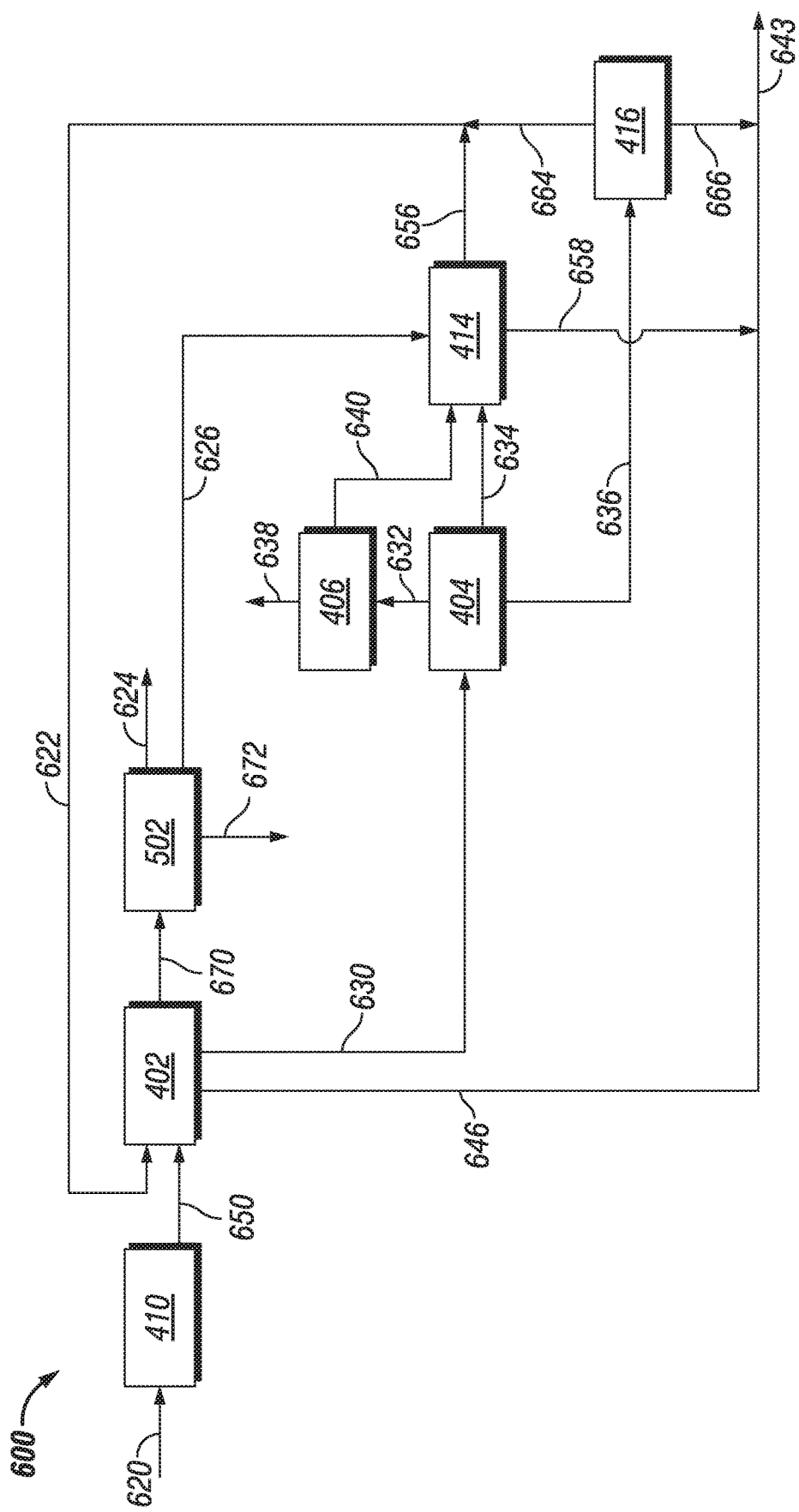
FIG. 6 is a process flow diagram for a dealkylation-transalkylation process for producing benzene and para-xylene from heavy reformate in the absence of hydrogen, in accordance with an embodiment of the disclosure.

FIG. 6 shows a process 600 for an embodiment of the dealkylation and transalkylation system for the production of benzene and para-xylene in the absence of hydrogen, in accordance with an embodiment of this disclosure. The process 600 includes a C9 dealkylation reactor 410, a reformate splitter 402, an aromatic extraction unit 502, a xylene splitter 404, a para-xylene separator 406, a transalkylation/isomerization reactor 414, and a C10+ dealkylation reactor 416. While the units of FIG. 6 are similar to those of FIGS. 3-5, FIG. 6 shows an embodiment where the aromatic extraction unit 502 is positioned downstream of the reformate splitter 402, and where no hydrogen supply is provided to the process 600.

A heavy reformate feed stream 620 including C6-C12+ aromatics (which can include coke precursors) is introduced into a C9 dealkylation reactor 410. The heavy reformate feed stream 620 can be a stream of reformate from a typical catalytic naphtha reformer. The heavy reformate feed stream 620 can be a stream of pyrolysis gasoline from a steam cracking furnace. The heavy reformate feed stream 620 can include non-aromatic hydrocarbons, such as naphthenes and paraffins, as well as aromatic hydrocarbons. The C9 dealkylation reactor 410 receives the heavy reformate feed stream 620 and produces a C9 dealkylation product stream 650. The C9 dealkylation reactor 410 is configured to selectively dealkylate C9-C12+ aromatics of the heavy reformate feed stream 620 to C6-C8+ aromatics. Also, the C9 dealkylation reactor 410 is configured to selectively crack compounds with two or more aromatic rings, such as naphthalene or derivatives of naphthalene, to produce BTX and light gases. The C9 dealkylation reactor 410 can be optimized to maximize the conversion of C9-12+ aromatics to benzene, toluene, and mixed xylenes. As a result, the C9 dealkylation product stream 650 includes converted C6-8+ aromatics from the dealkylation reaction and unconverted C6-8+ aromatics preexisting in the heavy reformate feed stream 620. The C9 dealkylation product stream 650 may include non-aromatic hydrocarbons, including light olefins such as ethylene, propylene, butylenes, pentenes, and dienes having four or five carbon atoms, produced as a byproduct of the dealkylation reaction or unreacted non-aromatic hydrocarbons preexisting in the heavy reformate feed stream 620. The C9 dealkylation product stream 650 may not include non-aromatic hydrocarbons having more than seven carbon atoms. In any case, coke precursors are removed by the dealkylation reaction.

The C9 dealkylation product stream 650 is introduced into a reformate splitter 402. The reformate splitter 402 is configured to separate C4− hydrocarbons (light olefins such as ethylene, propylene, butylenes, and 1,3-butadiene), C5-7 hydrocarbons (including aromatic and non-aromatic), and C8+ hydrocarbons (substantially aromatic) received from the C9 dealkylation product stream 650. Accordingly, a first light gas stream 646, a C5-7 product stream 670, and a C8+ aromatics product stream 630 are produced by the reformate splitter 402. The C8+ aromatics product stream 630 includes mixed xylenes. The first light gas stream 646 can include light olefins such as ethylene, propylene, butylenes, and 1,3-butadiene. One skilled in the art may select a suitable separation process for separating C4-, C5-7, and C8+ hydrocarbons from the C9 dealkylation product stream 650. For example, C4− hydrocarbons can be recovered from the top, C5-7 hydrocarbons can be recovered from the side, and C8+ hydrocarbons can be recovered from the bottom of a column. In some embodiments, the first light gas stream 646 is combined with a second light gas stream 658 and a third light gas stream 666 to form a light gas product stream 643. In some embodiments, the first light gas stream 646 can be further processed outside of the process 600.

The C5-7 product stream 670 is introduced into an aromatic extraction unit 502. The aromatic extraction unit 502 is configured to separate benzene, toluene, and C5-7 non-aromatic hydrocarbons received from the C5-7 product stream 670. Accordingly, a benzene product stream 624, a toluene product stream 626, and a non-aromatic product stream 672 are produced by the aromatic extraction unit 502. The non-aromatic product stream 672 includes non-aromatic hydrocarbons produced by the C9 dealkylation reactor 410. The non-aromatic product stream 672 is substantially free of aromatics. One skilled in the art may select a suitable separation process for extracting aromatics from the aromatic extraction unit 502. For example, chemical extraction or distillation, or a combination of the two, can be used to selectively separate the aromatics from the non-aromatics. One skilled in the art may select a suitable separation process for extracting benzene and toluene from the aromatics separated from the non-aromatics. In some embodiments, benzene can be extracted by solvent extraction. Toluene can be extracted by utilizing a fractionation column. In some embodiments, the non-aromatic product stream 672 can be further processed outside of the process 600.

The C8+ aromatics product stream 630 is introduced into a xylene splitter 404. The xylene splitter 404 is configured to separate C8 aromatics (mixed xylenes and ethylbenzene), any remaining C9 aromatics, and any remaining C10+ aromatics received from the C8+ aromatics product stream 630. Accordingly, a C8 aromatics product stream 632, a C9 aromatics product stream 634, and a C10+ aromatics product stream 636 are produced by the xylene splitter 404. One skilled in the art may select a suitable separation process for extracting C8 aromatics and C9 aromatics from the C8+ aromatics product stream 630. For example, C8 aromatics can be recovered from the top, C9 aromatics can be recovered from the side, and C10+ aromatics can be recovered from the bottom of a column.

The C8 aromatics product stream 632 is introduced into a para-xylene separator 406. The para-xylene separator 406 is configured to separate para-xylene received from the C8 aromatics product stream 632 including mixed xylenes (and ethylbenzene, if any). Accordingly, a para-xylene stream 638 and a ortho-/meta-xylene stream 640 are produced by the para-xylene separator 406. The ortho-/meta-xylene stream 640 includes ortho-xylene and meta-xylene. The ortho-/meta-xylene stream 640 is substantially free of para-xylene. One skilled in the art may select a suitable separation process for extracting para-xylene from the C8 aromatics product stream 632. For example, the para-xylene separator 406 can include an adsorptive process. The para-xylene separator 406 can include a crystallization process.

The C9 aromatics product stream 634, the ortho-/meta-xylene stream 640, and the toluene product stream 626 are introduced into the transalkylation/isomerization reactor 414. The transalkylation/isomerization reactor 414 is configured to receive C7-9 aromatics and produce benzene, toluene, mixed xylenes, and light gases. Via transalkylation, the transalkylation/isomerization reactor 414 is configured to convert toluene received from the toluene product stream 626 and C9 aromatics received from the C9 aromatics product stream 634 into mixed xylenes. In some embodiments, the C9 aromatics product stream 634 includes TMBs. Also via transalkylation, the transalkylation/isomerization reactor 414 is configured to convert toluene received from the toluene product stream 626 into benzene and mixed xylenes. Via isomerization, the transalkylation/isomerization reactor 414 is configured to convert ortho-/meta-xylene received from the ortho-/meta-xylene stream 640 into mixed xylenes by reestablishing the C8 aromatics thermodynamic equilibrium. Accordingly, a BTX product stream 656 is produced by the transalkylation/isomerization reactor 414. Because xylene isomerization is performed in the transalkylation/isomerization reactor 414, a separate transalkylation reactor or a separate isomerization reactor is not required.

In some embodiments, in the absence of hydrogen, the transalkylation/isomerization reactor 414 is configured to dealkylate alkyl groups of the received C7-9 aromatics to produce BTX and light gas. The produced BTX leaves the transalkylation/isomerization reactor 414 via the BTX product stream 656. In some embodiments, the BTX product stream 656 is added to the recycled product stream 622 to be reintroduced into the reformate splitter 402 for further separation. The produced light gas leaves the transalkylation/isomerization reactor 414 via a second light gas stream 658. The second light gas stream 658 can include light olefins such as ethylene and propylene. In some embodiments, the second light gas stream 658 is combined with the first light gas stream 646 the third light gas stream 666 to form a light gas product stream 643. In some embodiments, the second light gas stream 658 can be further processed outside of the process 600.

The C10+ aromatics product stream 636 is introduced into a C10+ dealkylation reactor 416. The C10+ dealkylation reactor 416 receives the C10+ aromatics product stream 636 and produces a C6-10 aromatics product stream 664. The C10+ dealkylation reactor 416 is configured to selectively dealkylate C10+ aromatics to C6-9 aromatics. Also, the C10+ dealkylation reactor 416 is configured to selectively crack compounds with two or more aromatic rings, such as naphthalene or derivatives of naphthalene, to produce BTX and light gases. Additionally, ethyl and propyl groups attached to the C10+ aromatics can form olefins such as ethylene and propylene. The C10+ dealkylation reactor 416 can be optimized to maximize the conversion of C10+ aromatics to BTX. As a result, the C6-10 aromatics product stream 664 includes converted C6-9 aromatics from the dealkylation reaction and unconverted C10 aromatics pre-existing in the C10+ aromatics product stream.

In some embodiments, in the absence of hydrogen, the C10+ dealkylation reactor 416 is configured to convert C10+ aromatics received from the C10+ aromatics product stream 636 into C6-9 aromatics and light gas. The produced light gas leaves the C10+ dealkylation reactor 416 via a third light gas stream 666. The third light gas stream 666 can include light olefins such as ethylene and propylene. In some embodiments, the third light gas stream 666 is combined with the first light gas stream 646 and the second light gas stream 658 to form a light gas product stream 643. In some embodiments, the third light gas stream 666 can be further processed outside of the process 600. In some embodiments, the C6-10 aromatics product stream 664 is added to the recycled product stream 622 to be reintroduced into the reformate splitter 402 for further separation.

This disclosure is illustrated by the following examples, which are presented for illustrative purposes only, and are not intended as limiting the scope of the invention which is defined by the appended claims.

shown in FIG. 1. The results are shown in Table 2. Stream numbers generally correspond to the reference labels shown in FIG. 1. The mass flow magnitudes of the chemical species are displayed in kilograms per hour (kg/hr). Bz, Tol, pX, MEB, and TMB refer to benzene, toluene, para-xylene, methylethylbenzene, and trimethylbenzene, respectively.

TABLE 2

| Stream No. | Total Mass Flow | $H_2$ | Light Gas | Bz | Tol | pX | pX-free C8 | MEB | TMB | C10+ |
|---|---|---|---|---|---|---|---|---|---|---|
| 120 | 1598 | 0.0 | 0.0 | 49.2 | 213.1 | 96.7 | 290.8 | 210.9 | 565.5 | 171.4 |
| 122 | 6992 | 0.0 | 0.0 | 67.2 | 591.4 | 1263.5 | 4360.8 | 2.5 | 641.4 | 65.4 |
| 124 | 73 | 0.0 | 0.0 | 72.9 | 0.0 | 0.0 | 0.0 | 0.0 | 0.0 | 0.0 |
| 126 | 964 | 0.0 | 0.0 | 0.0 | 964.3 | 0.0 | 0.0 | 0.0 | 0.0 | 0.0 |
| 127 | 955 | 0.0 | 0.0 | 0.0 | 954.6 | 0.0 | 0.0 | 0.0 | 0.0 | 0.0 |
| 128 | 10 | 0.0 | 0.0 | 0.0 | 9.6 | 0.0 | 0.0 | 0.0 | 0.0 | 0.0 |
| 129 | 10 | 0.0 | 0.0 | 4.0 | 0.3 | 1.7 | 3.7 | 0.0 | 0.0 | 0.0 |
| 130 | 7477 | 0.0 | 0.0 | 67.2 | 0.0 | 1382.1 | 4739.1 | 5.1 | 1144.7 | 138.5 |
| 132 | 6121 | 0.0 | 0.0 | 0.0 | 0.0 | 1382.1 | 4739.1 | 0.0 | 0.0 | 0.0 |
| 134 | 1150 | 0.0 | 0.0 | 0.0 | 0.0 | 0.0 | 0.0 | 5.1 | 1144.7 | 0.0 |
| 136 | 206 | 0.0 | 0.0 | 67.2 | 0.0 | 0.0 | 0.0 | 0.0 | 0.0 | 138.5 |
| 138 | 1382 | 0.0 | 0.0 | 0.0 | 0.0 | 1382.1 | 0.0 | 0.0 | 0.0 | 0.0 |
| 140 | 4739 | 0.0 | 0.0 | 0.0 | 0.0 | 0.0 | 4739.1 | 0.0 | 0.0 | 0.0 |
| 143 | 142 | 0.0 | 142.1 | 0.0 | 0.0 | 0.0 | 0.0 | 0.0 | 0.0 | 0.0 |
| 144 | 6 | 5.9 | 0.0 | 0.0 | 0.0 | 0.0 | 0.0 | 0.0 | 0.0 | 0.0 |
| 146 | 86 | 6.6 | 79.4 | 0.0 | 0.0 | 0.0 | 0.0 | 0.0 | 0.0 | 0.0 |
| 150 | 1449 | 0.0 | 0.0 | 0.0 | 372.8 | 118.6 | 378.3 | 2.5 | 503.3 | 73.1 |
| 152 | 6 | 5.9 | 0.0 | 0.0 | 0.0 | 0.0 | 0.0 | 0.0 | 0.0 | 0.0 |
| 156 | 2049 | 0.0 | 0.0 | 63.3 | 546.9 | 151.4 | 646.8 | 2.5 | 572.3 | 65.4 |
| 158 | 66 | 5.2 | 60.5 | 0.0 | 0.0 | 0.0 | 0.0 | 0.0 | 0.0 | 0.0 |
| 162 | 8 | 8.5 | 0.0 | 0.0 | 0.0 | 0.0 | 0.0 | 0.0 | 0.0 | 0.0 |
| 164 | 194 | 0.0 | 0.0 | 0.0 | 44.0 | 20.3 | 60.8 | 0.0 | 68.8 | 0.0 |
| 166 | 4 | 2.0 | 2.2 | 0.0 | 0.0 | 0.0 | 0.0 | 0.0 | 0.0 | 0.0 |
| 168 | 2 | 2.0 | 0.0 | 0.0 | 0.0 | 0.0 | 0.0 | 0.0 | 0.0 | 0.0 |

As shown in Table 2, comparing the mass flow magnitudes of the heavy reformate feed stream 120 and the C9 dealkylation product stream 150, the C9 dealkylation reactor 110 substantially reduces less useful C9-12+ aromatics, such as MEB, TMB, and C10+ aromatics, at the outset. Accordingly, quantities recovered in the C9 aromatics product stream 134 and the C10+ aromatics product stream 136 are minimal compared to the C8 aromatics product stream 132.

Advantageously, this example process shows that the C9-12+ aromatics are substantially removed by the C9 dealkylation reactor 110 at the outset, such that the toluene disproportionation unit 108, the transalkylation/isomerization reactor 114, and the C10+ dealkylation reactor 116 are minimally utilized. Also advantageously, lifetimes of the catalysts used in the C9 dealkylation reactor 110, the transalkylation/isomerization reactor 114, and the C10+ dealkylation reactor 116 are substantially improved due to the removal of coke precursors. Consequently, C6-12+ aromatics can be completely utilized to produce benzene, para-xylene, and light alkanes via the C9 dealkylation process, the transalkylation/isomerization process, and the C10+ dealkylation process.

Example 1

In accordance with at least one embodiment of this disclosure, an example process was simulated, similar to the process 100 shown in FIG. 1. The example process includes a C9 dealkylation reactor 110, a reformate splitter 102, a xylene splitter 104, a para-xylene separator 106, a toluene disproportionation unit 108, a PSA unit 112, a transalkylation/isomerization reactor 114, and a C10+ dealkylation reactor 116, generally corresponding to the components Example 2

In accordance with at least one embodiment of this disclosure, an example process was simulated, similar to the process 200 shown in FIG. 2. The example process includes a C9 dealkylation reactor 110, an aromatic extraction unit 202, a reformate splitter 102, a xylene splitter 104, a para-xylene separator 106, a PSA unit 112, a transalkylation/isomerization reactor 114, and a C10+ dealkylation reactor 116, generally corresponding to the components shown in FIG. 2. The results are shown in Table 3. Stream numbers generally correspond to the reference labels shown in FIG. 2. The mass flow magnitudes of the chemical species are displayed in kg/hr. Bz, Tol, pX, MEB, and TMB refer to benzene, toluene, para-xylene, methylethylbenzene, and trimethylbenzene, respectively.

114, and the C10+ dealkylation reactor 116 are substantially improved due to the removal of coke precursors. Consequently, C6-12+ aromatics can be completely utilized to produce benzene, para-xylene, and light alkanes via the C9 dealkylation process, the transalkylation/isomerization process, and the C10+ dealkylation process.

TABLE 3

| Stream No. | Total Mass Flow | $H_2$ | Light Gas & Paraffins | Bz | Tol | pX | pX-free C8 | MEB | TMB | C10+ |
|---|---|---|---|---|---|---|---|---|---|---|
| 220 | 1366 | 0.0 | 252.6 | 34.3 | 148.5 | 67.4 | 202.7 | 146.9 | 394.0 | 119.4 |
| 222 | 4634 | 0.0 | 0.0 | 42.6 | 390.0 | 839.7 | 2903.0 | 1.8 | 412.5 | 44.0 |
| 224 | 93 | 0.0 | 0.0 | 93.4 | 0.0 | 0.0 | 0.0 | 0.0 | 0.0 | 0.0 |
| 226 | 650 | 0.0 | 0.0 | 0.0 | 649.8 | 0.0 | 0.0 | 0.0 | 0.0 | 0.0 |
| 230 | 4951 | 0.0 | 0.0 | 0.0 | 0.0 | 922.3 | 3166.8 | 3.5 | 763.2 | 95.0 |
| 232 | 4089 | 0.0 | 0.0 | 0.0 | 0.0 | 922.3 | 3166.8 | 0.0 | 0.0 | 0.0 |
| 234 | 767 | 0.0 | 0.0 | 0.0 | 0.0 | 0.0 | 0.0 | 3.5 | 763.2 | 0.0 |
| 236 | 95 | 0.0 | 0.0 | 0.0 | 0.0 | 0.0 | 0.0 | 0.0 | 0.0 | 95.0 |
| 238 | 922 | 0.0 | 0.0 | 0.0 | 0.0 | 922.3 | 0.0 | 0.0 | 0.0 | 0.0 |
| 240 | 3167 | 0.0 | 0.0 | 0.0 | 0.0 | 0.0 | 3166.8 | 0.0 | 0.0 | 0.0 |
| 243 | 96 | 0.0 | 95.6 | 0.0 | 0.0 | 0.0 | 0.0 | 0.0 | 0.0 | 0.0 |
| 244 | 5 | 5.2 | 0.0 | 0.0 | 0.0 | 0.0 | 0.0 | 0.0 | 0.0 | 0.0 |
| 246 | 58 | 5.6 | 52.5 | 0.0 | 0.0 | 0.0 | 0.0 | 0.0 | 0.0 | 0.0 |
| 250 | 1063 | 0.0 | 2.6 | 50.8 | 259.8 | 82.7 | 263.8 | 1.8 | 350.7 | 50.9 |
| 252 | 5 | 5.2 | 0.0 | 0.0 | 0.0 | 0.0 | 0.0 | 0.0 | 0.0 | 0.0 |
| 256 | 1378 | 0.0 | 0.0 | 42.6 | 370.2 | 101.9 | 435.4 | 1.8 | 381.6 | 44.0 |
| 258 | 47 | 4.8 | 42.2 | 0.0 | 0.0 | 0.0 | 0.0 | 0.0 | 0.0 | 0.0 |
| 262 | 8 | 7.5 | 0.0 | 0.0 | 0.0 | 0.0 | 0.0 | 0.0 | 0.0 | 0.0 |
| 264 | 87 | 0.0 | 0.0 | 0.0 | 19.7 | 9.1 | 27.3 | 0.0 | 30.9 | 0.0 |
| 266 | 3 | 2.0 | 1.0 | 0.0 | 0.0 | 0.0 | 0.0 | 0.0 | 0.0 | 0.0 |
| 270 | 1060 | 0.0 | 0.0 | 50.8 | 259.8 | 82.7 | 263.8 | 1.8 | 350.7 | 50.9 |
| 272 | 253 | 0.0 | 252.6 | 0.0 | 0.0 | 0.0 | 0.0 | 0.0 | 0.0 | 0.0 |

As shown in Table 3, comparing the mass flow magnitudes of the heavy reformate feed stream 220 and the C9 dealkylation product stream 250, the C9 dealkylation reactor 110 substantially reduces less useful C9-12+ aromatics, such as MEB, TMB, and C10+ aromatics, at the outset. Accordingly, quantities recovered in the C9 aromatics product stream 234 and the C10+ aromatics product stream 236 are minimal compared to the C8 aromatics product stream 232.

Advantageously, this example process shows that the C9-12+ aromatics are substantially removed by the C9 dealkylation reactor 110 at the outset, such that the transalkylation/isomerization reactor 114 and the C10+ dealkylation reactor 116 are minimally utilized. Also advantageously, lifetimes of the catalysts used in the C9 dealkylation reactor 110, the transalkylation/isomerization reactor Example 3

In accordance with at least one embodiment of this disclosure, an example process was simulated, similar to the process 400 shown in FIG. 4. The example process includes a C9 dealkylation reactor 410, a reformate splitter 402, a xylene splitter 404, a para-xylene separator 406, a transalkylation/isomerization reactor 414, and a C10+ dealkylation reactor 416, generally corresponding to the components shown in FIG. 4. The results are shown in Table 4. Stream numbers generally correspond to the reference labels shown in FIG. 4. The mass flow magnitudes of the chemical species are displayed in kg/hr. Bz, Tol, pX, MEB, and TMB refer to benzene, toluene, para-xylene, methylethylbenzene, and trimethylbenzene, respectively.

TABLE 4

| Stream No. | Total Mass Flow | $H_2$ | Light Gas | Bz | Tol | pX | pX-free C8 | MEB | TMB | C10+ |
|---|---|---|---|---|---|---|---|---|---|---|
| 420 | 872 | 0.0 | 0.0 | 12.5 | 222.0 | 42.6 | 136.7 | 96.5 | 270.2 | 91.5 |
| 422 | 3870 | 0.0 | 0.0 | 90.2 | 283.1 | 708.5 | 2407.5 | 1.2 | 347.8 | 31.8 |
| 424 | 24 | 0.0 | 0.0 | 24.0 | 0.0 | 0.0 | 0.0 | 0.0 | 0.0 | 0.0 |
| 426 | 578 | 0.0 | 0.0 | 0.0 | 578.2 | 0.0 | 0.0 | 0.0 | 0.0 | 0.0 |
| 428 | 145 | 0.0 | 0.0 | 0.0 | 144.6 | 0.0 | 0.0 | 0.0 | 0.0 | 0.0 |
| 429 | 145 | 0.0 | 0.0 | 59.4 | 4.3 | 25.0 | 55.7 | 0.0 | 0.0 | 0.0 |
| 430 | 4101 | 0.0 | 0.0 | 90.2 | 0.0 | 761.6 | 2585.9 | 2.3 | 588.3 | 72.7 |
| 432 | 3348 | 0.0 | 0.0 | 0.0 | 0.0 | 761.6 | 2585.9 | 0.0 | 0.0 | 0.0 |
| 434 | 591 | 0.0 | 0.0 | 0.0 | 0.0 | 0.0 | 0.0 | 2.3 | 588.3 | 0.0 |
| 436 | 163 | 0.0 | 0.0 | 90.2 | 0.0 | 0.0 | 0.0 | 0.0 | 0.0 | 72.7 |
| 438 | 762 | 0.0 | 0.0 | 0.0 | 0.0 | 761.6 | 0.0 | 0.0 | 0.0 | 0.0 |
| 440 | 2586 | 0.0 | 0.0 | 0.0 | 0.0 | 0.0 | 2585.9 | 0.0 | 0.0 | 0.0 |
| 443 | 75 | 0.1 | 75.4 | 0.0 | 0.0 | 0.0 | 0.0 | 0.0 | 0.0 | 0.0 |
| 446 | 39 | 0.0 | 39.0 | 0.0 | 0.0 | 0.0 | 0.0 | 0.0 | 0.0 | 0.0 |
| 450 | 809 | 0.0 | 0.0 | 0.0 | 295.1 | 53.1 | 178.3 | 1.2 | 240.5 | 40.9 |
| 456 | 990 | 0.0 | 0.0 | 30.7 | 244.5 | 73.5 | 313.8 | 1.2 | 294.2 | 31.8 |

TABLE 4-continued

| Stream No. | Total Mass Flow | H2 | Light Gas | Bz | Tol | pX | pX-free C8 | MEB | TMB | C10+ |
|---|---|---|---|---|---|---|---|---|---|---|
| 458 | 35 | 0.0 | 34.7 | 0.0 | 0.0 | 0.0 | 0.0 | 0.0 | 0.0 | 0.0 |
| 464 | 151 | 0.0 | 0.0 | 0.0 | 34.3 | 15.8 | 47.4 | 0.0 | 53.6 | 0.0 |
| 466 | 2 | 0.1 | 1.7 | 0.0 | 0.0 | 0.0 | 0.0 | 0.0 | 0.0 | 0.0 |

As shown in Table 4, comparing the mass flow magnitudes of the heavy reformate feed stream 420 and the C9 dealkylation product stream 450, the C9 dealkylation reactor 410 substantially reduces less useful C9-12+ aromatics, such as MEB, TMB, and C10+ aromatics, at the outset. Accordingly, quantities recovered in the C9 aromatics product stream 434 and the C10+ aromatics product stream 436 are minimal compared to the C8 aromatics product stream 432.

Advantageously, this example process shows that the C9-12+ aromatics are substantially removed by the C9 dealkylation reactor 410 at the outset, such that the transalkylation/isomerization reactor 414 and the C10+ dealkylation reactor 416 are minimally utilized. Also advantageously, lifetimes of the catalysts used in the C9 dealkylation reactor 410, the transalkylation/isomerization reactor 414, and the C10+ dealkylation reactor 416 are substantially improved due to the removal of coke precursors. Consequently, C6-12+ aromatics can be completely utilized to produce benzene, para-xylene, and light alkanes via the C9 dealkylation process, the transalkylation/isomerization process, and the C10+ dealkylation process.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of forming para-xylene and benzene from a heavy reformate, the method comprising the steps of:
providing a heavy reformate feed stream, wherein the heavy reformate feed stream comprises C6-12+ aromatics;
reacting via dealkylation the heavy reformate feed stream to produce a C9 dealkylation product stream, wherein C9-12+ aromatics of the heavy reformate feed stream are selectively converted into C6-8+ aromatics, wherein the C9 dealkylation product stream comprises C6-8+ aromatics;
receiving and splitting the C9 dealkylation product stream to produce a benzene product stream, a toluene product stream, and a C8+ aromatics product stream;
receiving and splitting the C8+ aromatics product stream to produce a C8 aromatics product stream, a C9 aromatics product stream, and a C10+ aromatics product stream;
separating the C8 aromatics product stream to produce a para-xylene stream and an ortho-/meta-xylene stream, wherein the ortho-/meta-xylene stream comprises ortho-xylene and meta-xylene;
receiving and reacting via transalkylation the toluene product stream, the C9 aromatics product stream, and the ortho-/meta-xylene stream to produce a BTX product stream, wherein the BTX product stream comprises benzene, toluene, and mixed xylenes; and
receiving and reacting via dealkylation the C10+ aromatics product stream to produce a C6-10 aromatics product stream.

2. The method of claim 1, wherein the receiving and reacting via transalkylation step includes isomerizing ortho-xylene and meta-xylene of the ortho-/meta-xylene stream to produce para-xylene.

3. The method of claim 1, wherein olefins are produced in one or more steps selected from the group consisting of: the reacting via dealkylation step, the receiving and reacting via transalkylation step, and the receiving and reacting via dealkylation step.

4. The method of claim 3, wherein the olefins comprise ethylene and propylene.

5. The method of claim 1, wherein alkanes are produced in one or more steps selected from the group consisting of: the reacting via dealkylation step, the receiving and reacting via transalkylation step, and the receiving and reacting via dealkylation step.

6. The method of claim 5, wherein the alkanes comprise ethane and propane.

7. The method of claim 1, further comprising the step of:
providing a makeup hydrogen stream to one or more steps selected from the group consisting of: the reacting via dealkylation step, the receiving and reacting via transalkylation step, and the receiving and reacting via dealkylation step, to promote alkane production.

8. The method of claim 1, further comprising the steps of:
receiving a light gas produced from one or more steps selected from the group consisting of: the reacting via dealkylation step, the receiving and reacting via transalkylation step, and the receiving and reacting via dealkylation step, wherein the light gas comprises ethane, propane, and hydrogen; and
separating the light gas via pressure swing adsorption (PSA) to produce a light gas product stream and a hydrogen product stream, wherein the light gas product stream comprises ethane and propane.

9. The method of claim 8, wherein the reacting via dealkylation step includes providing the hydrogen product stream to promote alkane production.

10. The method of claim 8, wherein the receiving and reacting via transalkylation step includes providing the hydrogen product stream to promote alkane production.

11. The method of claim 1, wherein the receiving and splitting the C9 dealkylation product step includes receiving one or more selected from the group consisting of: the BTX product stream and the C6-10 aromatics product stream.

12. The method of claim 1, further comprising the step of:
receiving and reacting via disproportionation a portion of the toluene product stream to produce a toluene disproportionation product stream, wherein the toluene disproportionation product stream comprises benzene and mixed xylenes.

13. The method of claim 12, wherein the receiving and splitting the C9 dealkylation product step includes receiving the toluene disproportionation product stream.

14. The method of claim 1, further comprising the steps of:
receiving and separating the C9 dealkylation product stream to produce an aromatic product stream and a non-aromatic product stream; and
splitting the aromatic product stream to produce the C8 aromatics product stream, the C9 aromatics product stream, and the C10+ aromatics product stream.

15. The method of claim 1, wherein the receiving and splitting the C9 dealkylation product stream step includes producing a C4− light gas stream and a C5-7 product stream, wherein the C4− light gas stream comprises one selected from the group consisting of: ethane, ethylene, propane, propylene, butane, butylene, and 1,3-butadiene, and wherein the C5-7 product stream comprises benzene, toluene, and C5-7 non-aromatics.

16. The method of claim 15, further comprising the step of:
receiving and separating the C5-7 product stream to produce the benzene product stream, the toluene product stream, and a non-aromatic product stream, wherein the non-aromatic product stream comprises C5-7 non-aromatics.

17. A heavy reformate processing system for forming para-xylene and benzene, the heavy reformate processing system comprising:
a C9 dealkylation reactor, the C9 dealkylation reactor operable to receive a heavy reformate feed stream and to produce a C9 dealkylation product stream, wherein the heavy reformate feed stream comprises C6-12+ aromatics, wherein the C9 dealkylation reactor selectively dealkylates C9-12+ aromatics to C6-8+ aromatics, wherein the C9 dealkylation product stream comprises C6-8+ aromatics;
a reformate splitter fluidly coupled downstream of the C9 dealkylation reactor, the reformate splitter operable to receive the C9 dealkylation product stream and to produce a benzene product stream, a toluene product stream, and a C8+ aromatics product stream;
a xylene splitter fluidly coupled downstream of the reformate splitter, the xylene splitter operable to receive the C8+ aromatics product stream and to produce a C8 aromatics product stream, a C9 aromatics product stream, and a C10+ aromatics product stream;
a para-xylene separator fluidly coupled downstream of the xylene splitter, the para-xylene separator operable to receive the C8 aromatics product stream and to produce a para-xylene stream and an ortho-/meta-xylene stream, wherein the ortho-/meta-xylene stream comprises ortho-xylene and meta-xylene;
a transalkylation reactor fluidly coupled downstream of the reformate splitter, the xylene splitter, and the para-xylene separator, the transalkylation reactor operable to receive the toluene product stream, the C9 aromatics product stream, and the ortho-/meta-xylene stream, operable to produce a BTX product stream, wherein the BTX product stream comprises benzene, toluene, and mixed xylenes and is introduced into the reformate splitter, and operable to isomerize ortho-xylene and meta-xylene of the ortho-/meta-xylene stream to produce para-xylene; and
a C10+ dealkylation reactor fluidly coupled downstream of the xylene splitter, the C10+ dealkylation reactor operable to receive the C10+ aromatics product stream and to produce a C6-10 aromatics product stream, wherein the C6-10 aromatics product stream is introduced into the reformate splitter.

18. The heavy reformate processing system of claim 17, wherein the C9 dealkylation reactor, the transalkylation reactor, and the C10+ dealkylation reactor are operable to produce light gases including ethylene and propylene, in the absence of hydrogen.

19. The heavy reformate processing system of claim 17, wherein the C9 dealkylation reactor, the transalkylation reactor, and the C10+ dealkylation reactor are operable to produce light gases including ethane and propane, in the presence of hydrogen.

20. The heavy reformate processing system of claim 17, further comprising:
a pressure swing adsorption (PSA) unit, the PSA unit operable to receive ethane, propane, and hydrogen from the C9 dealkylation reactor, the transalkylation reactor, and the C10+ dealkylation reactor, and to produce a light gas product stream and a hydrogen product stream, wherein the light gas product stream comprises ethane and propane.

21. The heavy reformate processing system of claim 20, wherein the PSA unit is fluidly coupled upstream of the C9 dealkylation reactor and the transalkylation reactor, wherein the hydrogen product stream is passed to the C9 dealkylation reactor and the transalkylation reactor.

22. The heavy reformate processing system of claim 17, further comprising:
an aromatic extraction unit fluidly coupled downstream of the C9 dealkylation reactor and upstream of the reformate splitter, the aromatic extraction unit operable to receive the C9 dealkylation product stream and to produce an aromatic product stream and a non-aromatic product stream, wherein the aromatic product stream is introduced into the reformate splitter.

23. The heavy reformate processing system of claim 17, wherein the reformate splitter is operable to produce a C4− light gas stream and a C5-7 product stream, wherein the C4− light gas stream comprises one selected from the group consisting of: ethane, ethylene, propane, propylene, butane, butylene, and 1,3-butadiene, and wherein the C5-7 product stream comprises benzene, toluene, and C5-7 non-aromatics.

24. The heavy reformate processing system of claim 23, further comprising:
an aromatic extraction unit fluidly coupled downstream of the reformate splitter and upstream of the transalkylation reactor, the aromatic extraction unit operable to receive the C5-7 product stream and to produce the benzene product stream, the toluene product stream, and a non-aromatic product stream, wherein the non-aromatic product stream comprises C5-7 non-aromatics, wherein the toluene product stream is introduced into the transalkylation reactor.

* * * * *